(12) United States Patent
DeVera et al.

(10) Patent No.: US 6,495,723 B1
(45) Date of Patent: Dec. 17, 2002

(54) ZEOLITE SUPPORT LOADED WITH A BASE MATERIAL FOR USE IN THE COUPLING OF ANILINE AND NITROBENZENE

(75) Inventors: Antonio L. DeVera, Avon; Roger Keranan Rains, Richfield, both of OH (US)

(73) Assignee: Flexsys America, Akron, OH (US)

( * ) Notice: Subject to any disclaimer, the term of this patent is extended or adjusted under 35 U.S.C. 154(b) by 0 days.

(21) Appl. No.: 09/598,155

(22) Filed: Jun. 21, 2000

(51) Int. Cl.$^7$ .......................... C07C 209/48; B01J 29/00
(52) U.S. Cl. .................. 564/419; 564/420; 564/421; 564/422; 564/423; 502/77; 502/150; 502/172; 502/200
(58) Field of Search .................. 564/419, 420, 564/421, 422, 423; 502/77, 150, 172, 200

(56) References Cited

U.S. PATENT DOCUMENTS

| | | | |
|---|---|---|---|
| 3,393,066 A | 7/1968 | Mayer | 75/26 |
| 3,847,990 A | 11/1974 | Blahak | 260/576 |
| 4,122,118 A | 10/1978 | George et al. | 260/576 |
| 4,140,716 A | 2/1979 | Maender et al. | 260/562 R |
| 4,155,936 A | 5/1979 | Sturm | 260/576 |
| 4,178,315 A | 12/1979 | Zengel et al. | 260/647 |
| 4,187,248 A | 2/1980 | Merten et al. | 260/576 |
| 4,187,249 A | 2/1980 | Maender et al. | 260/576 |
| 4,196,146 A | 4/1980 | Merten et al. | 260/576 |
| 4,209,463 A | 6/1980 | Maender et al. | 260/576 |
| 4,404,401 A | 9/1983 | Zengel et al. | 564/416 |
| 4,463,191 A | 7/1984 | D'Sidocky et al. | 564/398 |
| 4,479,008 A | 10/1984 | Batorewicz et al. | 564/433 |
| 4,518,803 A | 5/1985 | Batorewicz et al. | 564/410 |
| 4,614,817 A | 9/1986 | Maender et al. | 564/406 |
| 4,670,595 A | 6/1987 | Podder et al. | 564/406 |
| 4,683,332 A | 7/1987 | Sturm | 564/414 |
| 4,760,186 A | 7/1988 | Solodar | 564/415 |
| 4,900,868 A | 2/1990 | Merten et al. | 564/398 |
| 5,117,063 A | 5/1992 | Stern et al. | 564/398 |
| 5,420,354 A | 5/1995 | Malz et al. | 564/423 |
| 5,453,541 A | 9/1995 | Stern et al. | 564/398 |
| 5,977,411 A | * 11/1999 | De Vera | 564/397 |

FOREIGN PATENT DOCUMENTS

| | | | |
|---|---|---|---|
| EP | 0 863 130 | 9/1998 | C07C/209/36 |
| GB | 1 440 767 | 6/1976 | C07C/85/11 |

OTHER PUBLICATIONS

Ayyanger, et al., *Tetrahedron Letters*, vol. 31, No. 22, pp. 3217–3220, 1990.
Banerjee, et al., *J. Chem. Soc. Chem. Comm*, 18, 1275–1276, 1988.
A. Wohl et al., *Concerning the Effect of Nitrobenzene on Aniline in the Presence of Alkali*, pp. 1–7, Translation from German.
A. Wohl, et al. *Chemishe Berichte*, pp. 2442–2450, 1901.
Stern, M., et al., *Journal of the American Chemical Society, Direct Coupling of Aniline and Nitrobenzene: A New Example of Nucleophilic Aromatic Subsitution for Hydrogen*, vol. 114, No. 23, 1992.
A. Wohl, *Chemische Berichte*, 36, pp. 4135–4139, 1903.
A. Wohl, *Toward the Knowledged of the Reaction Between Nitrobenzene and Aniline in the Presence of Alkali.*

* cited by examiner

*Primary Examiner*—Brian J. Davis
(74) *Attorney, Agent, or Firm*—Louis A. Morris

(57) ABSTRACT

This invention provides a composition suitable for use in a reaction zone where aniline is reacted with nitrobenzene to obtain intermediates of 4-aminodiphenylamine comprising a solid support having interior channels with base material employed in the reaction loaded into the channels. The cross-sectional dimensions of the channels are such as to provide a restricted transition state with regard to the reaction and to improve the selectivity of the reaction in favor of the intermediates. The invention also provides a method for loading the base material in the solid support. The invention further provides a process for carrying out the above reaction using the above composition.

59 Claims, 12 Drawing Sheets

Phenazine Formation: Free Base

Restricted Phenzaine Formation in ZSM-5

ONE-STEP/ONE-POT PROCESS

Pd-Z = Pd on ZSM-5

ZEOLITE SUPPORT LOADED WITH A BASE MATERIAL FOR USE IN THE COUPLING OF ANILINE AND NITROBENZENE

BACKGROUND OF THE INVENTION

This invention relates to a support loaded with a base material, its method of manufacture and a process in which it is used for making 4-aminodiphenylamine (4-ADPA), an important intermediate in the production of substituted para-phenylenediamine (PPD) antidegradants for polymers, especially rubber.

It is known to prepare 4-ADPA by way of a nucleophilic aromatic substitution mechanism, wherein an aniline derivative replaces halide. This method involves preparation of a 4-ADPA intermediate, namely 4-nitrodiphenylamine (4-NDPA) followed by reduction of the nitro moiety. The 4-NDPA is prepared by reacting p-chloronitrobenzene with an aniline derivative, such as formanilide or an alkali metal salt thereof, in the presence of an acid acceptor or neutralizing agent, such as potassium carbonate, and, optionally, utilizing a catalyst. See, for example, U.S. Pat. Nos. 4,187,248; 4,683,332; 4,155,936; 4,670,595; 4,122,118; 4,614,817; 4,209,463; 4,196,146; 4,187,249; 4,140,716. This method is disadvantageous in that the halide that is displaced is corrosive to the reactors and appears in the waste stream and must therefore be disposed of at considerable expense. Furthermore, use of an aniline derivative such as formanilide, and use of p-chloro-nitrobenzene, requires additional manufacturing equipment and capabilities to produce such starting materials from aniline and nitrobenzene, respectively.

It is also known to prepare 4-ADPA from the head-to-tail coupling of aniline. See, for example, G.B. 1,440,767 and U.S. Pat. No. 4,760,186. This method is disadvantageous in that the yield of 4-ADPA is not acceptable for a commercial process. It is also known to decarboxylate a urethane to produce 4-NDPA. See U.S. Pat. No. 3,847,990. However, such method is not commercially practical in terms of cost and yield.

It is known to prepare 4-ADPA by hydrogenating p-nitrosodiphenylhydroxylamine which can be prepared by catalytic dimerization of nitrosobenzene utilizing, as a reducing agent, aliphatic compounds, benzene, naphthalene or ethylenically unsaturated compounds. See for example, U.S. Pat. Nos. 4,178,315 and 4,404,401. It is also known to prepare p-nitrosodiphenylamine from diphenylamine and an alkyl nitrate in the presence of excess hydrogen chloride. See, for example, U.S. Pat. Nos. 4,518,803 and 4,479,008.

It is also known to produce 4-nitrosodiphenylamine by reacting acetanilide and nitrobenzene in DMSO in the presence of sodium hydroxide and potassium carbonate at 80° C. for 5 hours. See Ayyangar et al., Tetrahedron Letters, Vol. 31, No. 22, pp. 3217–3220 (1990). However, the yield of 4-nitrosodiphenylamine is low and is therefore not commercially practical. Furthermore, such method requires utilization of an aniline derivative, namely, acetanilide, and therefore increases the cost of the starting materials.

The production of 4-nitrosodiphenylamine in very low yield, by reacting aniline with nitrobenzene has long been known to the art. See Wohl, Chemische Berichte, 36, p. 4135 (1903) and Chemische Berichte, 34, p. 2442 (1901).

It is also known to prepare 4-ADPA by the successive steps of a) reacting aniline with nitrobenzene in the presence of a base, under controlled conditions to produce a mixture containing the salts of 4-nitrodiphenylamine and of 4-nitrosodiphenylamine and then b) hydrogenating the salts. U.S. Pat. Nos. 5,117,063 and 5,453,541 disclose such a process.

U.S. Pat. No. 5,420,354, shows another process for the preparation of p-aminodiphenylamine by contacting nitrobenzene with hydrogen and aniline in the presence of a hydrogenation catalyst, a hydrogenation inhibitor and an acid catalyst. While this latter process is described as a one-step process, selectivity to the desired product is relatively low.

The process of the present invention produces an intermediate of 4-ADPA or 4-ADPA directly in a novel manner employing a zeolite support loaded with a base material.

SUMMARY OF THE INVENTION

In one embodiment, the invention comprises a composition suitable for use in a reaction zone where aniline is reacted with nitrobenzene to obtain intermediates of 4-aminodiphenylamine. The composition comprises a solid support having interior channels with base material employed in the reaction loaded into the channels. The cross-sectional dimensions of the channels are such as to provide a restricted transition state with regard to the reaction and to improve the selectivity of the reaction in favor of the intermediates.

In another embodiment, where the above solid support is a zeolite, the invention comprises a method of making the above composition comprising:
(a) ion exchanging zeolite with base material by contacting the zeolite with an aqueous solution of the base material;
(b) drying the zeolite recovered from step (a);
(c) adding additional base material in aqueous solution to the dried zeolite from step (b) to obtain zeolite slurry; and
(d) recovering zeolite from the zeolite slurry having the desired loading of base material.

In a further embodiment, this invention provides a process for preparing an intermediate of 4-ADPA by reacting aniline with nitrobenzene in a reaction zone containing a solid upport loaded with a base material. The solid support has interior channels with base material employed in the reaction loaded into the channels. The cross-sectional dimensions of the channels are such as to provide a restricted transition state with regard to the reaction and to improve the selectivity of the reaction in favor of the intermediate.

In still another embodiment, the present invention is a one-step process for preparing 4-aminodiphenylamine (4-ADPA) comprising charging nitrobenzene into a reaction zone under hydrogen pressure and in the presence of a base material loaded on a solid support and a hydrogenation catalyst. The solid support has interior channels with base material employed in the reaction loaded into the channels. The cross-sectional dimensions of the channels are such as to provide a restricted transition state with regard to the reaction and to improve the selectivity of the reaction in favor of 4-ADPA.

An yet another embodiment, the invention is a process for the hydrogenation of nitrobenzene to 4-aminodiphenylamine (4-ADPA) comprising:

a) preparing a reaction zone by supplying a strong organic base loaded on a solid support and a hydrogenation catalyst, the solid support having interior channels with base material employed in the reaction loaded into the channels; the cross-sectional dimensions of the channels are such as to provide a restricted transition state with regard to the reaction and to improve the selectivity of the reaction in favor of 4-ADPA;

b) applying a flow of hydrogen at a pressure sufficient to force the conversion of nitrobenzene to 4-ADPA intermediates and to further hydrogenate the intermediates to 4-ADPA;

(c) charging to the reaction zone an amount of aniline and nitrobenzene such that the molar ratio of aniline to nitrobenzene in the reaction zone is not greater than about 5.0, and that the molar ratio of nitrobenzene to the strong organic base is not greater than about 18.0; and (d) conducting the hydrogenation reaction for the conversion of nitrobenzene to 4-ADPA as a one-step process.

Other embodiments of the present invention encompass further details relating to the composition of loaded solid support, methods of making the loaded support and conditions and process details concerning the use of the loaded support, all of which are hereinafter disclosed in the following discussion of each of those facets of the invention.

DETAILED DESCRIPTION OF THE INVENTION

Figure 1:
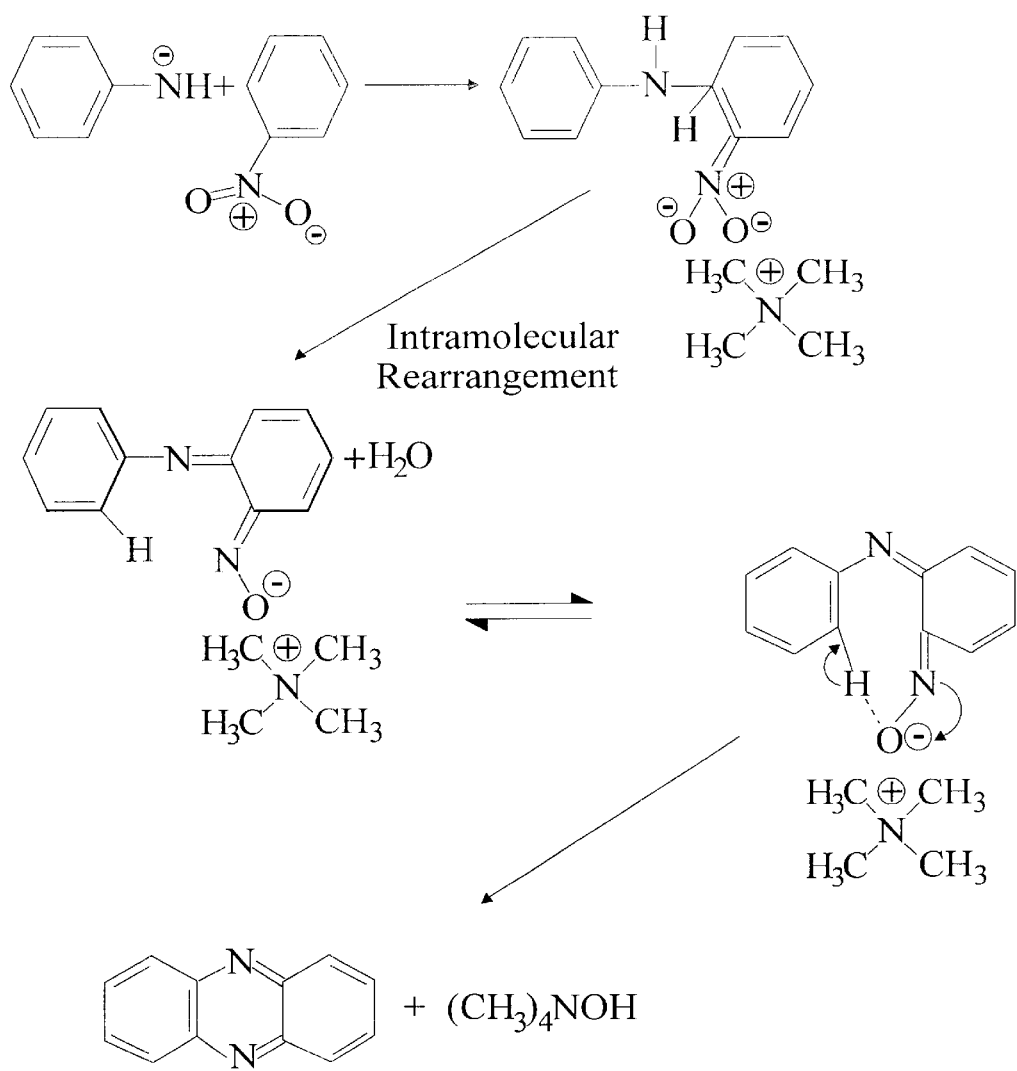
FIG. 1 shows the free base ortho-attack of the anilide salt of nitrobenzene.

In the tetramethylammonium hydroxide TMA(OH)-assisted coupling of aniline and nitrobenzene, the selectivity to 4-nitrosodiphenylamine (4-NODPA) and 4-nitrodiphenylamine 4-NDPA) is a function of the amount of water and the aniline to nitrobenzene ratio. Stern et al (Stern, M., Hilemen, F.D., and Bashkin, J.K. JACS, 1992, 14) suggested that the effect of too much water present appears to inhibit the formation of the anilide ion. In order that these factors lessen its effects, the work leading to the present invention probed into improving the selectivity of 4-NODPA and 4-NDPA using a zeolite framework as a matrix for impregnating TMA(OH), although the concept of the invention in its broadest sense, would employ any solid support having interior channels with cross-sectional dimensions being such as to provide a restricted transition state with regard to the aniline/nitrobenzene reaction.

The impregnation or loading of TMA(OH) leads to reduced levels of water which would indicate a marked increase in selectivity. Furthermore, if a suitable zeolite framework is chosen, other by-products such as phenazine, and even azobenzene may be eliminated because of the molecular-shape selective zeolites. The shape-selectivity arises from restricted transition state, where due to steric hindrance, bulkier molecules, such as phenazine, are prevented from forming within the restricted intracrystalline channels/cavity of certain zeolites.

The subject method for producing intermediates of 4-ADPA comprises charging nitrobenzene to a reaction zone, and in the presence of a suitable base loaded on a zeolite support.

Suitable bases include, but are not limited to, inorganic bases such as, for example, hydroxide such as lithium hydroxide, sodium hydroxide, cesium hydroxide and potassium hydroxide, including mixtures thereof. Preferred are strong organic bases, such as potassium t-butoxide and alkoxides, including $C_1$–$C_6$-alkoxides, and quaternary ammonium hydroxides and the like, and organic bases selected from the group of tetra substituted ammonium hydroxides, each substituent of which may be independently selected from alkyl, aryl or arylalkyl groups, aryl trialkylammonium hydroxides, arylalkyl trialkylammonium hydroxides and alkylsubstituted diammonium hydroxides.

Preferred materials for use as bases are tetraalkylammonium hydroxides such as tetramethylammonium hydroxide (TMA(OH)). The amount of base utilized in the present process can vary over a wide range and is dependent, for example, on, among other factors, the degree to which a specific reaction product is desired to be enhanced or minimized. For example, the reaction can be conducted in a manner which is limiting in base or the reaction can be conducted in a manner which is limiting in nitrobenzene or aniline. It is preferred that the base be used in an amount sufficient to achieve a molar ratio of nitrobenzene to TMA (OH) of not greater than about 18.

Phase transfer catalysts may be used in conjunction with the above base source. Phase transfer catalysts include aryl, alkyl and aryl alkyl ammonium salts, crown ethers and the like, and amine bases, such as lithium bis(trimethylsilyl) amide, and mixtures thereof.

The favorable selectivity and conversion of the reaction is achieved by loading of the strong base on an appropriate solid support. This effectively eliminates the production of unwanted by-products and increases selectivity and conversion to 100% on both counts. An appropriate solid support is one having interior channels with cross-sectional dimensions being such as to provide a restricted transition state with regard to the coupling reaction and to improve the selectivity of the reaction in favor of the intermediates of 4-ADPA. Suitable supports are pillared clays, aluminosilicates and silica alumina phosphates. From that group, a zeolite support may be used. Suitable zeolite materials, which may be used and be expected to generate equally good selectivity and conversion results include mordenites, highly siliceous ZSM-5 type materials (high silicon to aluminum ratio zeolites), beta zeolites and expanded clays such as montomorillonite that are propped by agents such as metals. Of these, the class of ZSM-5 type and mordenites are preferred.

Zeolite ZSM-5 is a unique class of alumino silicates with a crystal structural framework consisting of two types of intersecting channels: a straight type channel with elliptical openings of 0.51 to 0.58 that runs parallel to the b-axis of the orthorhombic unit cell. The other type has a near circular channel with 0.54 to 0.56 nm openings that is sinusoidal (zigzag) and directed along the z-axis. The crystal structure building block is a pentasil unit with 10-membered oxygen rings. The channels in the framework intersect in a manner that offers a larger space of about 0.9 nm.

If on the hypothesis that the deposition of TMA(OH) occurs by pore-filling, the role of diffusion can further enhance the product ratio, 4-NODPA/4-NDPA. In the diffusion process, the mole ratio of aniline to nitrobenzene is perhaps larger compared to when TMA(OH) is unsupported by a zeolite framework, especially when nitrobenzene is limited as in a dropwise addition to the aniline ion within the restricted intracrystalline channel.

The base component may be added as TMA(OH) loaded on a zeolite support. For purposes of the remainder of this application, reference will be made to the use of the ZSM-5 zeolite, which is a preferred embodiment. This is not, however, intended to be limiting thereto in any manner as other zeolites are equally well suited for use herein as stated above.

The TMA(OH)/ZSM-5 system functions as a coupling agent for the coupling reaction of nitrobenzene to aniline, and as stated above, results in enhanced selectivity. The use of the TMA(OH)-loaded ZSM-5 eliminates the formation of phenazine and reduces the azobenzene yield. This is significant given the carcinogenic character of phenazine, which is difficult to separate from the product and may thus require costly post-reaction removal. The reaction instead produces 4-nitrosodiphenylamine and 4-nitrodiphenylamine. Further, the ratio of 4-nitrosodiphenylamine to 4-nitrodiphenylamine is increased, the importance of which is seen in that the 4-nitrosodiphenylamine intermediate is more easily and readily hydrogenated to 4-ADPA, as compared to the hydrogenation of 4-nitrodiphenylamine.

Figure 2:
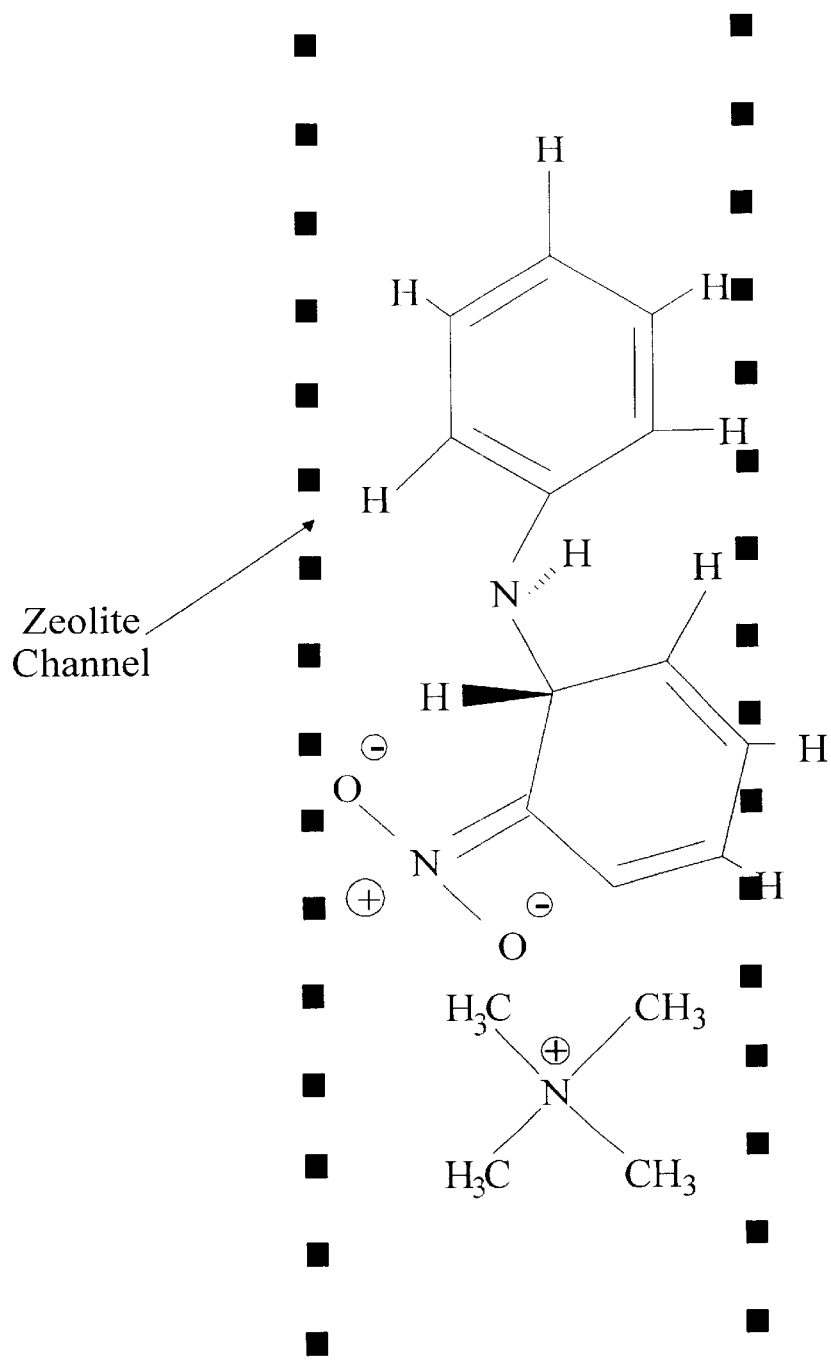
FIG. 2 shows a conformation of a transition state of phenazine that nearly fits the is ZSM-5 channel.

A successful loading of TMA(OH) onto ZSM-5 will eliminate the formation of phenazine and significantly reduce the formation of azobenzene. In accordance with the present invention, the loading allows the TMA(OH) to fill in the pore channels of ZSM-5. The pore channels have dimensions of about 5 to 6 Angstroms and can accommodate reactions that have kinetic diameters that will properly match these dimensions. Products that proceed through a transition state that effectually produce a compound larger than the kinetic diameter of the ZSM-5 channels are prevented. FIG. 1 shows the free base ortho-attack of the anilide salt on nitrobenzene. All of these conformations are relatively stable but yet have kinetic diameters that are larger than that allowed for in ZSM-5 pore channels. FIG. 2 shows a conformation of a transition state of phenazine that nearly fits the ZSM-5 channel. This refers to TMA(OH) loaded onto a ZSM-5 pore channel. There are two aspects here: 1.) this transition state requires a large activation energy so that, in all probability, this transition state may be difficult to form, and 2.) the kinetic diameter of this transition state is slightly larger than the pore size due largely to the structure of the molecule.

Figure 3:
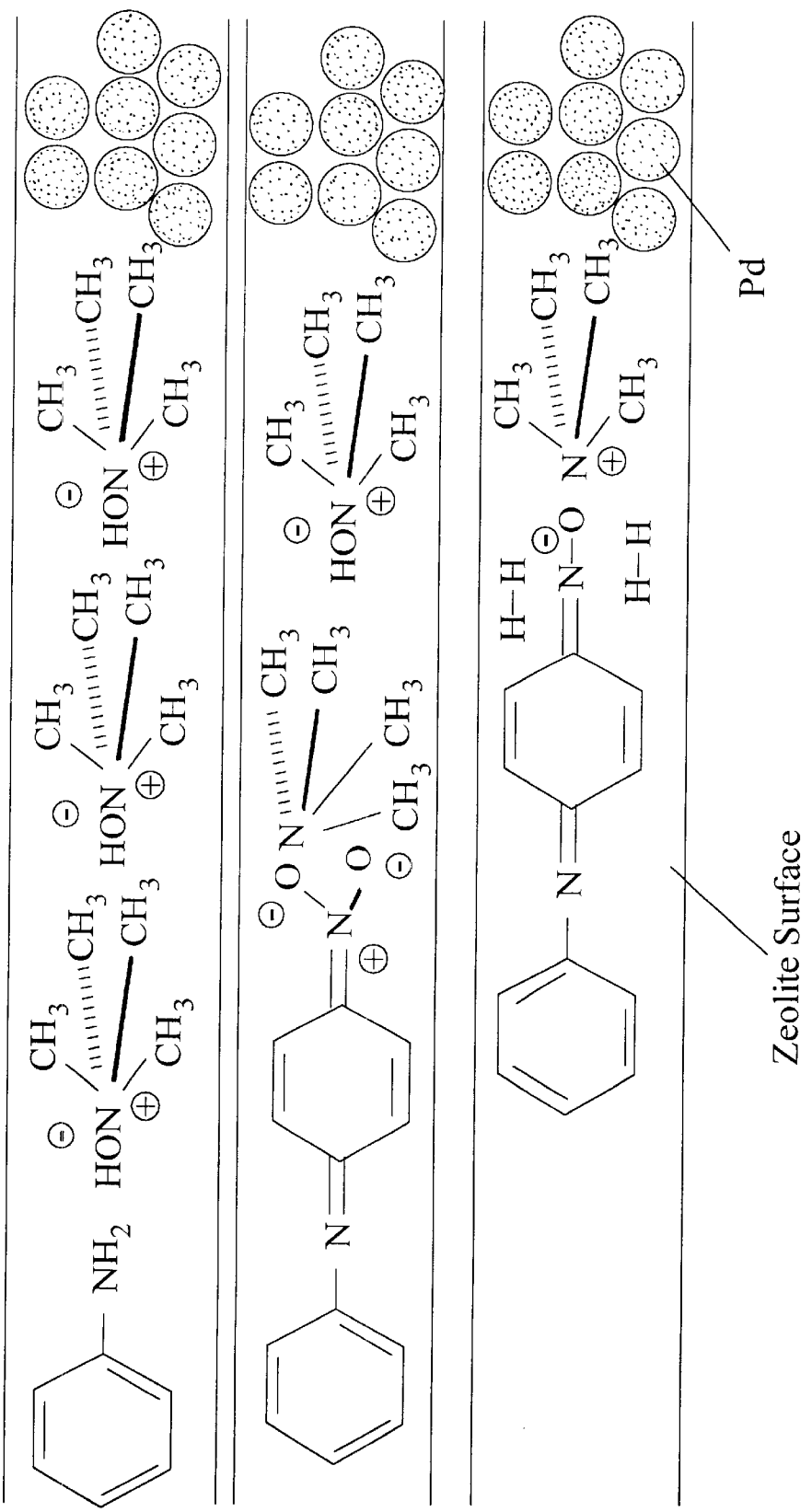
FIG. 3 shows the Meisenheimer salt of nitrobenzene formed in the ZSM-5 channel.

The technique of loading TMA(OH) into a protonated zeolite is unique and careful attention to procedure is important especially at higher loadings. Without intending to be bound to any particular theory, it is conjectured that the coupling reaction proceeds by formation of the anilide salt inside the channel. With nitrobenzene, the Meisenheimer salt is formed inside the channel as well (see FIG. 3.) The surface areas of pores are larger than those external to the zeolite. Azobenzene is formed at very low levels and it is believed that this formation is due to TMA(OH) that is located external to the zeolite crystal surface (not in the pores).

Figure 4:
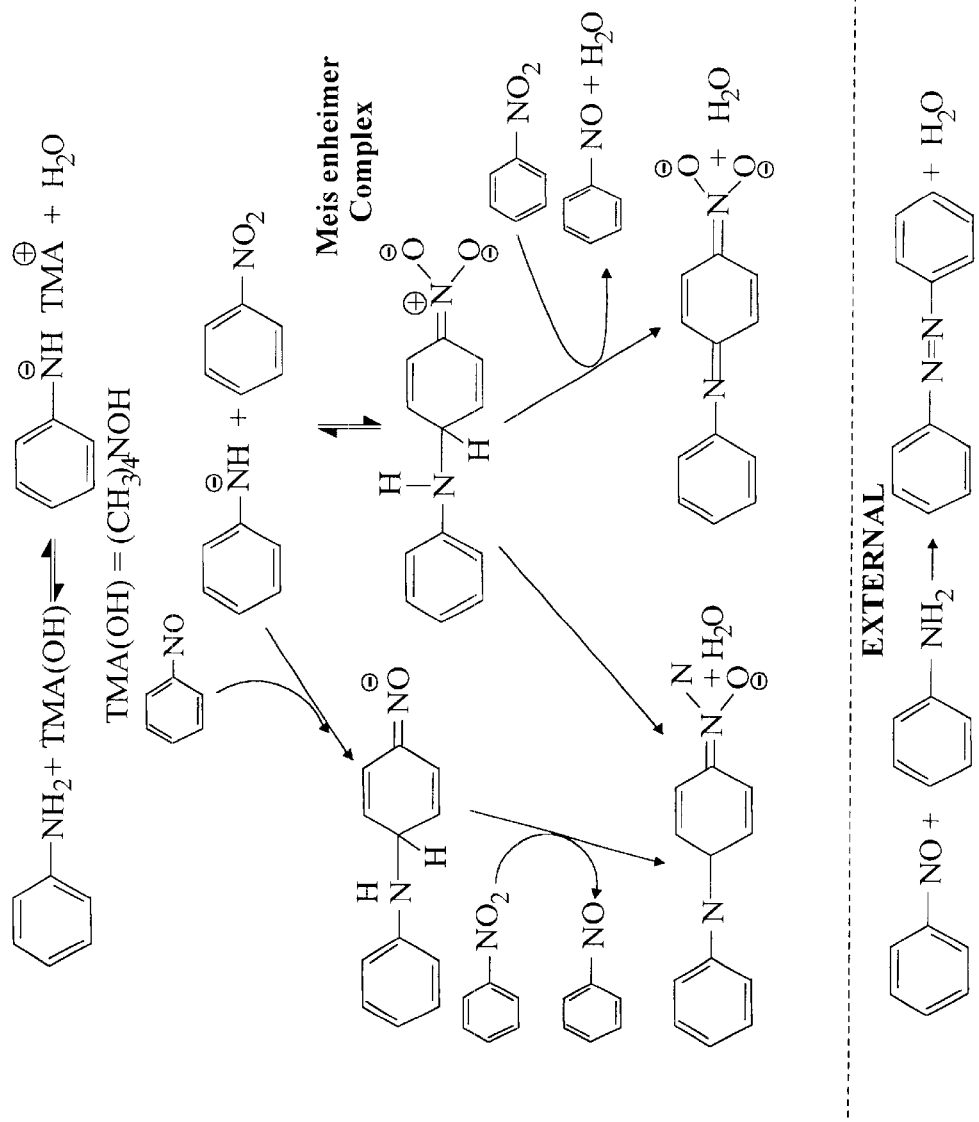
FIG. 4 shows the reaction of an anilide salt with nitrosobenzene in the intracrystalline channel to form the tetramethylammonium salt of 4-NODPA.

The high ratio of 4-NODPA/4-NDPA is due to two kinetic pathways that lead to formation of 4-NODPA. FIG. 4 shows that within the intracrystalline channel the anilide salt can react with nitrosobenzene to form the tetramethylammonium salt of 4-NODPA. This path diverts the formation of azobenzene where, in the presence of free base, nitrosobenzene reacts with aniline. In the intracrystalline channel, the probability that aniline is present is small because, inside this channel, aniline forms quickly to form the anilide salt—where the ratio of TMA(OH) to aniline is high during the first few minutes of the reaction and remains fiairly high throughout the reaction until all TMA(OH) has been tied to the salt.

The ZSM-5 zeolite provides still another advantage over the use of the TMA(OH) alone. TMA(OH) is generally prone to decomposition to trimethylamine and methanol, especially in the absence of water. Base decomposition is undesireable for reasons which include the abatement of decomposed products such as trimethylamine and methanol. Further considerations related to the cost of TMA(OH) make up are also of importance. The ZSM-5 support, however, stabilizes the TMA(OH) and eliminates this unwanted decomposition.

It is possible to achieve 100% selectivity and 100% conversion using the TMA(OH)/ZSM-5 system. This represents an improvement over the use of TMA(OH) without the zeolite support, which still achieved good selectivity at about 95–96%. The improved results have been achieved using a 15 wt. % loading of TMA(OH) on a ZSM-5 zeolite support. It is expected that a TMA(OH) loading not greater than about 25 wt. % will afford similarly positive results. Loading greater than 25% can cause structural collapse of the zeolite structure. The higher loading is preferred because it will require less reactor volume. It will also be relatively easy to keep the solids suspended. For similar production requirements as the free base, low loadings will increase the solids content and cause difficulty in maintaining solids suspension and mixing. Loading amounts will likely depend on the silicon to aluminum ratio. It is conjectured that at higher silicon to aluminum ratios, the loading may be higher than 25% without obtaining structural collapse. ZSM-5, in particular, can be prepared with high silicon to aluminum ratio.

It is important when using this system that the TMA(OH) be loaded onto the ZSM-5 support prior to addition to the reaction zone. Straight addition of ZSM-5 to a mixture of aniline, nitrobenzene and TMA(OH) does not produce the same selectivity as the TMA(OH) loaded ZSM-5. The anilide salt formed reacts readily with nitrobenzene to form the Meisenheimer complex and its diffusion rate in the intracrystalline channel is relatively slow. Similarly, the rate of ortho attack of the anilide salt on nitrobenzene to form phenazine is relatively faster than the diffusive rate. Therefore a simple addition of the zeolite on the coupling reaction mixture will not offer any advantage.

To affect the aspect ratio (reaction mixture height/diameter) of the reaction mixture which is important to control the extent of solids settling in the reactor, a diluent or solvent may be employed in the process of the invention, provided that it does not extract the base from the solid support. The only solvent known to be suitable is aniline. An amount of aniline in excess of that needed for the reaction may be charged to the reaction zone, in which case this excess of aniline serves as the solvent.

The loading of the base on ZSM-5 is non-trivial. Loading is accomplished by:

(a) ion exchanging zeolite with base material by contacting the zeolite with an an aqueous solution of base material;

(b) drying zeolite recovered from step (a);

(c) adding additional base material in aqueous solution to the dried zeolite from step (b) to obtain zeolite slurry; and (d) recovering zeolite from said zeolite slurry having the desired loading of base material.

A successful procedure for loading is repeatable and depends on several factors:

i.) Ion exchange

Typically, not greater than about 40° C. and an ion exchange solution not greater than about 15 wt. % TMA (OH) are suitable. Temperatures and TMA(OH) concentration greater than these will accelerate destruction of the crystals and increase base decomposition.

ii.) Level of loading

Loading at 25 wt. % seemed to be the limit for the ZSM-5 shown in the examples and it is suspected that this is dependent on the silicon to aluminum ratio. The solution used for loading should contain not greater than about 28 wt. % TMA(OH).

iii.) Drying of the base/zeolite crystals.

Drying is preferred at 40° C. in the presence of nitrogen as a vector gas. Drying temperatures greater than 40° C. and overdrying may result in structural collapse. It is preferred that the dried base loaded material have a water to base mole ratio of from about 2.0 to about 5.0. When dry, base/zeolite crystals are kept in dry nitrogen. Once the crystals are loaded and properly dried, temperatures up to 180° C. may be tolerated.

The process of the present invention may be practiced in two steps which employ two reaction zones, in the first zone a condensation reaction in which intermediates of 4-ADPA are generated, followed by a catalytic hydrogenation reaction in the second zone that produces 4-ADPA. The process may also be carried out in one step in which 4-ADPA is generated directly from a single reaction zone. The following discussion applies to both the two step and one step processes, unless one step is specifically stated or clearly implied.

With regard to the one step process, as the nitrobenzene is hydrogenated it generates aniline in situ, which reacts with a portion of the nitrobenzene to produce 4-ADPA intermediates, specifically salts of 4-nitrodiphenylamine (4-NDPA) and 4- nitrosodiphenylamine (4-NODPA), among other reaction products. The hydrogenation reaction further converts these 4-NDPA and 4-NODPA intermediates to 4-ADPA as the reaction proceeds. The capability to achieve 4-ADPA in a one-step, or one-pot, reaction process is advantageous. A key to obtaining high yield and selectivity to 4-aminodiphenylamine is to push the reaction to make more aniline; otherwise, the yield of nitrobenzene is lost to azoxybenzene or another step will be required to recover aniline from azoxybenzene as in the catalytic hydrogenation of azoxybenzene.

Alternatively, for producing 4-ADPA it is possible to enhance the intermediate (4NDPA and 4-NODPA) generation by introducing a separate charge of aniline to the reaction zone simultaneously with the nitrobenzene. For producing alkylated PPD, of which 4-ADPA is an intermediate, the subject method includes the further step of hydrogenating the 4-ADPA intermediates to effect conversion to 4-ADPA. Further, for producing alkylated p-phenylenediamines the subject method includes the step of reductively alkylating the 4-ADPA produced above to obtain the alkylated PPD, an antidegradant/antiozonant for polymers, particularly rubber.

Several factors are identified as having a benefit in optimization of the process provided herein for the conversion of nitrobenzene to 4-ADPA. A primary factor is loading of the strong organic base on a zeolite support. Use of the base in this manner results in one-hundred percent (100%) conversion. Another factor involves control of the molar ratio of nitrobenzene to the TMA(OH) base material. This ratio should be no greater than about 18.0. With regard to the one step process, at higher nitrobenzene: TMA(OH) molar ratios the hydrogenation reaction to produce 4-ADPA is unfavorably affected in that the selectivity shifts to formation of azoxybenzene, aniline and diphenylhydrazine rather than selectivity to 4-aminodiphenylamine.

One more factor which can be controlled to affect optimization of 4-ADPA yield and selectivity is the molar ratio of aniline to nitrobenzene available in the reaction zone. The molar ratio of aniline to nitrobenzene can vary from a large excess of nitrobenzene to a large excess of aniline. Preferably, the reaction is conducted utilizing an excess of aniline, but not less than a molar ratio of aniline to nitrobenzene of about 5.0. The ratio of 4-NDPA to 4-NODPA produced in the reaction of the present invention can be controlled by varying the ratio of aniline to nitrobenzene. For example, the higher the ratio of aniline to nitrobenzene, the higher the ratio of 4-NODPA to 4-NDPA.

Preferable in the one-step process embodiment is the charging of nitrobenzene, and aniline if charged, in the presence of hydrogen, to achieve a molar ratio of aniline to nitrobenzene also not less than about 5.0. This is preferable because control of selectivity to higher levels of 4-ADPA can be easily achieved. However, with excess amounts of nitrobenzene, given the proper level of hydrogenation catalyst, some amount of nitrobenzene will be lost to nitrobenzene reduction products, i.e., azoxybenzene, azobenzene, and diphenylhydrazine. In addition to the foregoing factors, essential to the one-step process embodiment is conducting the process under hydrogen pressure. The hydrogen pressure in the reaction zone mentioned herein provides a driving force to effect hydrogenation during the method of the invention. For very active hydrogenation catalysts, such as those classified as noble metals, the gauge pressure is preferably between 0 and 7000 kPa under either hydrogen flow control or pressure control. The rate of hydrogen uptake during flow control is equally important in affecting the selectivity to 4-nitrosodiphenyl-amine, and eventually to 4-aminodiphenylamine. The flow rate used will be dependent upon the type and level of catalyst.

Also included in the one step embodiment of the process of the invention is the use of a hydrogenation catalyst, including the choice of hydrogenation catalyst, the amount of catalyst and the level of the catalyst on the support. Hydrogenation catalysts are well known in the art. There are a variety of catalyst types that are appropriate as reduction catalysts for the present invention. Among these are at least one of copper, silver-magnesium oxide, copper-cerium oxide, copper-manganese oxide, iron-manganese oxide, platinum, nickel, molybdenum, sulfided noble metals, palladium, rhodium, ruthenium, iridium and platinum. The metal may be present on a suitable support selected from the group consisting of alumina, pumice, silica, activated carbon, and carbon black, and the catalyst may be separate from the base loaded zeolite.

More particularly, preferred catalysts include copper on alumina or pumice;

silver-magnesium oxide on pumice; copper-cerium oxide on pumice; copper- manganese oxide or iron-manganese oxide on pumice; copper on silica; platinum on activated carbon or carbon black; nickel on silica or kieselguhr; molybdenum or palladium on carbon or alumina using catalyst inhibitors such as thiophene, thiourea, triphenyl phosphite, polyamines, magnesium oxide, morpholine, and thioethers; and sulfided noble metal catalysts using sulfiding agents such as hydrogen sulfide, sodium sulfide, ammonium sulfide, and dimethyl sulfoxide. The choice of catalyst should be that which retards or inhibits the direct hydrogenation of nitrobenzene to a terminal product, such as azoxybenzene.

Use of catalysts will result in larger hydrogen uptake which consequently promotes the reduction of nitrobenzene to unwanted by-products such as azoxybenzene, which lowers the selectivity to 4-ADPA. In such a catalytic system, the flow can be regulated to lower pressures (such as those lower than 700 kPa) and higher levels of tetramethylammonium hydroxide, TMA(OH), which consequently increase the yield of nitrobenzene to 4-ADPA.

Ideally, rather than being separate, the catalyst will be associated with the loaded solid support. The solid support may comprise a cylindrical extrudate having a hollow section along its longitudinal axis with the remainder of the extrudate comprising a structure with base loaded interior channels, the hollow section being loaded with the hydrogenation catalyst. The hydrogenation catalyst may comprise free metal loaded into the interior channels of the solid support with the base material.

The invention, as described hereinabove, allows for the production of 4-ADPA with only nitrobenzene, hydrogen, an organic base and an hydrogenation catalyst as starting materials. The reaction events, such as the head-to-tail coupling of aniline and nitrobenzene and the hydrogenation of the salts of 4-NODPA and 4-NDPA to 4-ADPA, need not be separated. Also, given the proper choice of molar ratios of aniline to nitrobenzene and nitrobenzene to organic base, and the proper weight ratio of organic base to hydrogenation catalyst, optimal selectivity to 4-ADPA can be achieved without continuous removal of protic material, such as water. Protic material removal can, however, enhance selectivities in some reaction modes. These factors are advances over the invention of U.S. Pat. No. 5,453,541, referred to hereinabove.

In the present invention, protic removal is not necessary so long as the requirements are satisfied for increased selectivity to 4-ADPA, which includes choosing the proper aniline to nitrobenzene and nitrobenzene to organic base molar ratios and the weight ratios of organic base to the hydrogenation catalyst. In the present invention, the water removal can be effected to further improve the selectivity using a different reactor set up, such as a continuous fixed bed of hydrogenation catalyst where the water removal does not require vacuum conditions. Also, the production of 4-ADPA in the present invention requires elevated pressures without significant regard to the removal of the protic material, such as water.

The process of the invention may be carried out with nitrobenzene charged to the reaction zone gradually over a period of time sufficient to achieve high selectivity to 4-ADPA and a charge of aniline is charged to the reaction zone initially with the nitrobenzene. The nitrobenzene may be charged to the reaction zone gradually, over a period of time, usually over from 0.1 to 10 hours. The temperature in the action zone is preferably 90° C., and is held isothermally. The hydrogen gauge pressure at either flow or pressure control is 0 to about 3000 kPa, gauge At constant hydrogen pressure, near the end of the process, the pressure might be lower than 5.0 kPa, gauge.

Preferably, in a semi-batch mode, nitrobenzene can be charged over time to achieve the highest possible selectivity to 4-ADPA. In this mode, the amount of organic base, such as TMA(OH), relative to nitrobenzene is larger, and with an appropriate amount of hydrogenation catalyst present, a higher selectivity to 4-ADPA can be obtained. The end point for the reaction is determined by the amount of water produced in the coupling reaction, because at high water content the head-to-tail coupling of aniline and nitrobenzene is diminished and the reaction shifts to favor the formation of azoxybenzene.

The selectivity to 4-ADPA can also be enhanced by manipulating the hydrogen flow control so that the head-to-tail coupling of aniline and nitrobenzene is effected against the direct hydrogenation of nitrobenzene to the terminal product, such as azoxybenzene. This hydrogenation flow rate is controlled so that the pressure is in the lower portion of the range.

The process may be carried out in batch mode with the entire charge of nitrobenzene supplied to the reaction zone at one time.

The process of the invention may also be carried out as a continuous process with a fixed bed of hydrogenation catalyst fed continuously with a charge of excess aniline, nitrobenzene, hydrogen and with the base material loaded on a solid support.

While nitrobenzene and aniline (if used) are recited as reactants, the method is also applicable to the use of nitrobenzene, nitrosobenzene or substituted aniline derivatives, including compounds containing one or more nuclear substituents which do not interfere with the reaction.

As used herein, the term "substituted aniline derivatives" means aniline containing one or more electron withdrawing or electron releasing substituents on the aromatic ring. Applicable substituents include, but are not limited to, halides, —$NO_2$, —$NH_2$, alkyl groups, alkoxy groups, —$SO_3$, —COOH and aryl, aralkyl or alkaryl groups containing at least one —$NH_2$ group. Halides are selected from the group consisting of chloride, bromide and fluoride. The preferred alkyl and alkoxy groups contain from 1 to about 6 carbon atoms. The preferred aryl, aralkyl and alkaryl groups contain from about 6 to about 18 carbon atoms. Examples of substituted aniline derivatives include, but are not limited to, 2-methoxyaniline, 4-methoxyaniline, 4-chloroaniline, p-toluidine, 4-nitroaniline, 3-bromoaniline, 3-bromo-4-aminotoluene, p-aminobenzoic acid, 2,4-diaminotoluene, 2,5-dichloroaniline, 1,4-phenylene diamine, 4,4'-methylene dianiline, 1,3,5-triaminobenzene and mixtures thereof.

The reaction comprising the one-step process is conducted at a suitable temperature that can vary over a wide range. For example, the temperature can fall within a range of from about 20° C. to about 180° C., such as from about 80° C. to about 100° C., preferably from about 80° C. to about 90° C. A most preferred temperature for conducting the reaction of the present invention is from about 80° C. to about 90° C., such as at 85° C.

In the two step process, the preferred temperature in the first step reaction can fall within a range from about 10° C. to about 150° C. and in the second step from about 50° C. to about 150° C.

Figure 5:
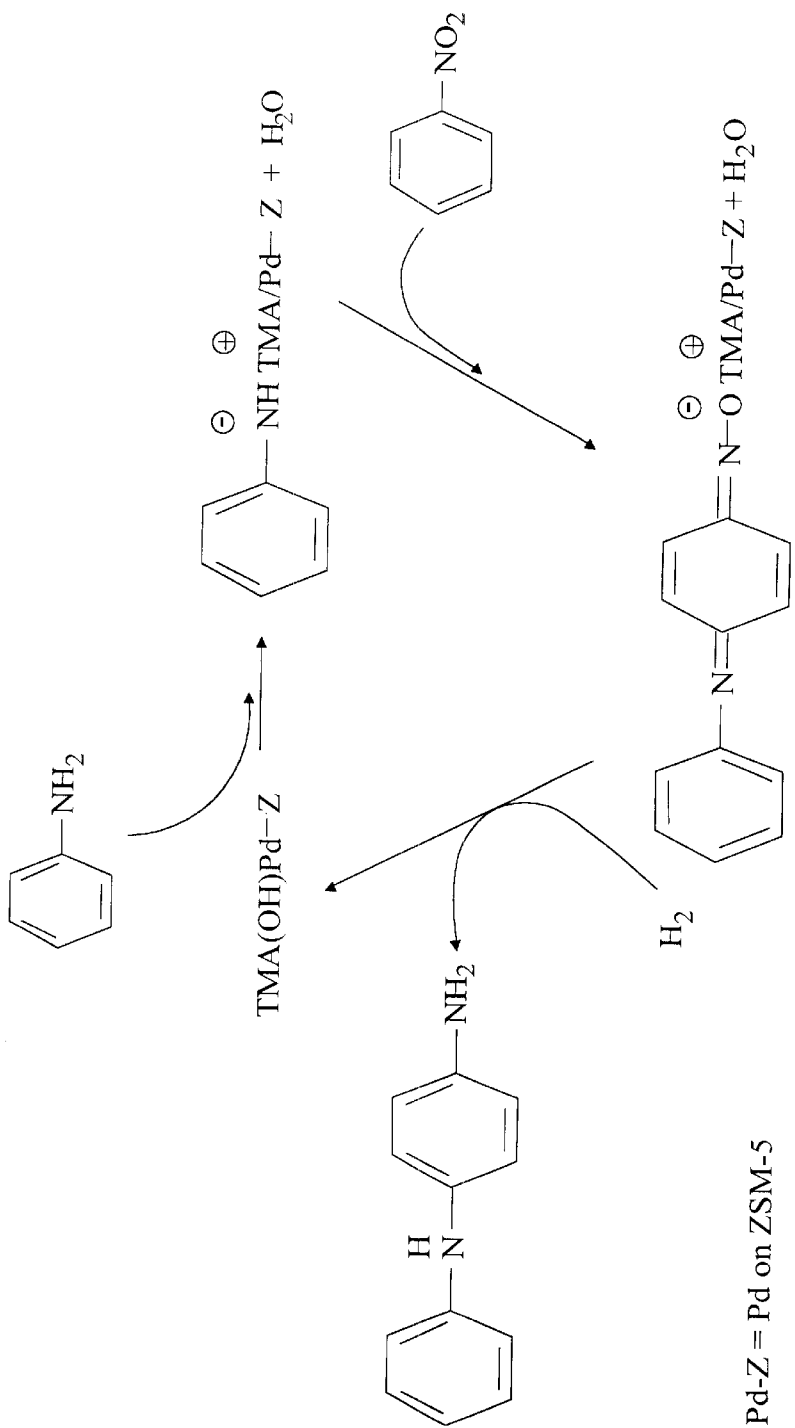
FIG. 5 shows a one-step/one-pot process for TMA(OH) regeneration.

TMA(OH) is regenerated in the one-step process. This scheme is cyclic in nature as depicted in FIG. 5. For the base loaded on Pd/Zeolite ZSM-5 (Pd supported on ZSM-5), the regeneration of TMA(OH) can be effective as it may not need recovery using a centrifugal liquid/liquid extractor. The design of the base (TMA(OH)) loaded on Pd/Zeolite will require a configuration such that the base should encapsulate the Pd/Zeolite. Pd loading on the zeolite is such that it is highly dispersed.

Reductive alkylation of 4-ADPA to produce antiozonants can be conducted by any one of several well known methods. See, for example, U.S. Pat. No. 4,900,868. Preferably, 4-ADPA and a suitable ketone or aldehyde are reacted in the presence of hydrogen and platinum-on-carbon as catalyst. Suitable ketones include methylisobutyl ketone (MIBK), acetone, methylisoamylketone and 2-octanone. It should be noted that reduction of the 4-ADPA intermediates and alkylation of the reduced material can be conducted in the same reaction vessel utilizing the ketone as a solvent. See, for example, U.S. Pat. No. 4,463,191, and Banerjee et al, J. Chem. Soc. Chem. Comm. 18, 1275–76 (1988).

Contemplated equivalents of the reactants and reagents set forth above are reactants and reagents otherwise corresponding thereto and having the same general properties wherein one or more of the various groups, e.g., $NO_2$, are simple variations. In addition, where a substituent is designated as, or can be, a hydrogen, the exact chemical nature of a substituent which is other than hydrogen at that position is not critical so long as it does not adversely affect the overall activity and/or synthesis procedure.

The chemical reactions described above are generally disclosed in terms of their broadest application to the method of this invention. Occasionally, the reaction conditions may not be applicable as specifically described to each reactant and reagent within the disclosed scope. For example, certain suitable bases may not be as soluble in one solvent as they are in other solvents. The reactants and reagents for which this occurs will be readily recognized by those skilled in the art. In all such cases, either the reactions can be successfully performed by conventional modifications known to those skilled in the art, e.g., by appropriate adjustments in temperature, pressure and the like, by changing to alternative conventional reagents such as other solvents or other bases, by routine modification of reaction conditions, and the like, or other reactions disclosed herein or otherwise conventional, will be applicable to the method of this invention. In all preparative methods, all starting materials are known or are readily preparable from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In this work, zeolite ZSM-5 was employed because of its unique intracrystalline pore structure, where it is supposed that crystals of TMA(OH) dihydrate are encapsulated. It is interesting to note that in the synthesis of ZSM-5, the organic base tetrapropylammonium hydroxide was utilized as a template for creating the unique crystal structure. Hence, it was anticipated that TMA(OH) would be encapsulated inside the ZSM-5 channels.

As a test of the hypothesis of shape selectivity for loaded ZSM-5, a series of experiments were conducted to determine if a simple addition of a calcined ZSM-5 to base followed by the regular coupling reaction scheme will do the same as the loaded counterpart. It was found that the selectivity resulting from simple addition is about the same as the unloaded TMA(OH), or that a simple addition of the zeolite in the coupling reaction mixture did not improve the selectivity. Recognizing the selectivity benefits of a TMA(OH) impregnated ZSM-5, the technique of a successful loading becomes important, since such procedures are not trivial. In determining a good loading procedure, a prepared batch of loaded material was subjected to a coupling reaction test. The same batch was also subjected to TGA and IR analysis for characterization.

Experiments

TMA(OH) Loading

The ZSM-5 used in the experiments were the ammonium form (from PQ Corporation/CBV 5000 series). Other forms, such as protonated or sodium form would be just as acceptable. Two silicon to aluminum ratios (Si/Al) were used e.g., 50 and 150. The coupling experiments, however, did not show effects of the Si/Al ratio on the product selectivity and conversion. The low Si/Al ratio denotes a more acidic zeolite and are found to be slightly more prone to structural collapse, especially if the loaded TMA(OH) is "overdried".

Prior to loading, these zeolites were calcined using the following temperature programming in a muffle furnace that was equipped with a continuous flow of air: 50° C./min to 400° C., 180 min at 400° C., ramp to 450° C. at 10° C./min, 180 min at 450° C., 180 min at 450° C. The calcination was done to convert the ammonium form to the protonated form of ZSM-5 and at the same time burn off the organics that were not removed in the zeolite synthesis. The temperature was capped at 450° C. to prevent the zeolite structure from disintegration via a thermal dealumination process which involves the conversion of a Bronsted acid type zeolite to a Lewis acid type zeolite and where dehydroxylation had occurred.

There were three loading techniques that were used and the one that is described here was the most successful one, since the other techniques tended to yield partial to complete intracrystalline structural collapse of the zeolite. The existence of a zeolite matrix structural collapse (referred to later as structural collapse) is evidenced by physical inspection of the dried loaded material. A good loading would typically show a consistently homogeneous solid phase, while those loadings which exhibited partial structural collapse showed two solid phases. It is surmised that the two solid phases constitute a zeolite loaded phase and amorphous TMA(OH) silicate/aluminate.

A complete structural collapse is easily observed especially during the filtration of the TMA(OH)/zeolite slurry where the slurry is found to consist of a gelatinous emulsion. Structural collapse may be characterized for a thoroughly water-washed loaded ZSM-5 by X-ray diffraction patterns (Cu-K α) relative to an unloaded ZSM-5.

Structurally collapsed zeolite, even if it is partial, is not advantageous. As evidenced in the following series of loading/coupling reaction experiments, a structurally collapsed material would always yield azobenzene and phenazine. In the process of loading, the calcined ZSM-5 was ion exchanged at 40° C. using 5 to 1 5 wt. % aqueous TMA (OH). The ion-exchange lasted about 3 to 4 hours (for a batch of 160 gms of ZSM-5). The zeolite slurry was vacuum filtered and then vacuum dried overnight at 40° C. with flowing nitrogen.

The dried ion-exchanged material was weighed. From this weight, the appropriate amount of from about 5 to about 25 (w) % TMA(OH) was added to make-up a slurry of not greater than about 38% solids to achieve the desired loading. Water was then evaporated from the zeolite slurry under vacuum conditions and a water bath at a temperature not exceeding about 40° C. A rotary evaporator that was equipped with a vacuum pump was found as an ideal evaporation apparatus. After evaporation, the moist zeolite cake underwent further drying under a 40° C. vacuum (desiccator) and with a continuous flow of nitrogen.

The dried loaded material was not subjected to water washing since this would have leached out TMA(OH) which had been "pore-filed" in the intracrystalline channels. It is believed that the amount of TMA(OH) that was deposited on the external surface area of the zeolite was comparatively smaller than the amount of TMA(OH) encapsulated within the intracrystalline channels.

The above method was developed based on the observations of a series of loading/coupling experiments. The following factors believed to cause structural collapse were deduced from these experiments:

a.) Vacuum evaporation of water at high temperature. It was concluded that because of possibilities of localized hot spots on the surface of the reaction vessel, direct electrical heating is not recommended. A hot water bath at 40° C. was sufficient.

b.) Loading of TMA(OH) greater than 25 weight percent of ion-exchanged ZSM-5.

c.) Over drying. Typically, the TMA(OH) in the zeolite matrix should correspond to the dihydrate form, otherwise, the final dried material forms a very hard mass that is very difficult to break into smaller particles (or powder form). The overdried material has a physical form that has resemblance to a hard candy-like material.

d.) Unmixed zeolite slurry during the evaporation step. Mixing is important for proper loading. An unmixed slurry, when dried, would result in zeolite crystals that are TMA(OH) silicate/aluminate rich on the external surface.

The method of the invention may be completely understood by reference to the following examples.

Examples of Loading

TMA(OH) Loading Example No.1

151.8 gms of appropriately calcined and protonated ZSM-5 was added to 121.4 gms of 25% TMA(OH) and 151.8 ml of deionized water. Mixing for ion exchange was for three hours at 40° C. The slurry was filtered through a Buchner funnel. The filter cake was collected and the filtrate reused for subsequent loading. 213.7 gms of 25% aqueous TMA(OH) was added and the slurry was mixed vigorously for 30 minutes at 30° C. on a hot plate. The resulting slurry was placed in a flat evaporating dish and dried in a vacuum desiccator using a nitrogen purge. Drying was maintained at 40° C. for two and one half hours. The resulting dried sample was in one solid phase that was easy to grind. The ground sample was a fluffy material and when used in the coupling reaction of aniline and nitrobenzene did not produce phenazine.

TMA(OH) Loading Example No. 2

Effect of Excessive Drying Time and Ion Exchange Temperature 116.0 gm of calcined and protonated ZSM-5 was added to a solution of 92.8 gms of 25% aqueous TMA(OH) and 116 ml of deionized water. The resulting slurry was ion exchanged for about 4 hours at 48° C. The slurry was filtered in a Buchner funnel. The filter cake was dried at 40° C. in a vacuum desiccator for fourteen hours and the filtrate set aside for use in subsequent loading. To the dried filter cake was added 122.7 gms of 25% aqueous TMA(OH). The resulting slurry was vigorously mixed at 40° C. for 30 minutes and dried in a vacuum desiccator for 72 hours with no inert gas purge. An additional 48 hours of drying at room temperature yielded a very hard solid material that was very difficult to grind. The ground solid consisted of what appeared to be two solid phases. A coupling reaction of aniline and nitrobenzene using the ground material from this preparation produced appreciable levels of phenazine.

TMA(OH) Loading Example No. 3

Excess TMA(OH)

A slurry solution was made up of 50 gms of calcined and protonated ZSM-5, 45 gms of 25% aqueous TMA(OH) and 300 ml of deionized water. The resulting solution was dried overnight at about 40 to 44 C. using a continously stirred vessel heated with an electric hot plate. The resulting solution was a thick slurry and most of the water was dried out. The thick slurry was transferred to a vacuum desiccator to dry further for about three hours. The vacuum desiccator was kept at 40° C. with a nitrogen purge. The dried material was hard and appeared to have another continous solid layer.

To the dried material, 350 ml of deionized water was added, mixed vigorously and filtered through a Buchner funnel. The top layer was a shiny white layer of solid material. The bottom portion, primarily ZSM-5 appeared to be dull white in color. The top layer—about 8 gms, was treated further with addition of about 30.5 gms of 25% aqueous TMA(OH) and 300 ml of deionized water. The loading was done for four hours at about 45° C. The resulting slurry was filtered and then dried in a vacuum desiccator for twenty four hours at 42° C. The dried material showed two layers of solid. The material, although it was not hard and therefore easier to grind failed the coupling reaction test which consisted of reacting aniline and nitrobenzene in that it produced significant amounts of phenazine. It is estimated that the material used in the coupling reaction test had a TMA(OH) content of about 33 wt. %. It is apparent that TMA(OH) loading at such a high level causes the ZSM-5 crystal structure to collapse.

TMA(OH) Loading Example No. 4

Use of Hot Water Bath for Drying 86.24 gms of 25% aqueous TMA(OH) was added to 102.8 ml of deionized water. 107.8 gm of calcined and protonated ZSM-5 was added to form a slurry that was mixed vigorously at 40° C. for 3 hours and 15 minutes. The ion-exchanged material was filtered. The filtrate was kept aside for use in subsequent loadings. To make a 20% loading of TMA(OH) in the zeolite, 154.8 gms of 25% by weight of aqueous TMA(OH) was added to the cake. The resulting slurry was transferred to a rotary evaporator. The temperature of the heating medium was controlled at 40° C. and the rotary evaporator was equipped with a vacuum pump. The drying time was adjusted depending on the vacuum pressure at given temperature. It is preferred to run the drying temperature of not nore than 80° C. The most suitable temperature is 40° C. to reduce the level of TMA(OH) decomposition. For this example, the pressure was controlled at 13 mm Hg at 40° C. Drying was allowed to proceed for about an hour and 10 minutes. The resulting material produced a thick paste that was flowable. This material was transferred to a flat evaporating dish and allowed to further dry at about 35° C. for 15 hours in a vacuum desiccator. The dried solid was not hard and very easy to grind. The coupling reaction test, which consists of reacting aniline and nitrobenzene did not produce phenazine using the above prepared material.

TMA(OH) Loading Example No. 5

An ion exchange mixture was prepared of 90.6 gms of 25% aqueous TMA(OH), 1 13 ml of of deionized water and 1 13.2 gm of calcined and protonated ZSM-5. The ion-exchange was carried out at 40° C. with vigorous mixing for about three hours. The tetramethylammonium ZSM-5 was filtered and the filtrate was reused for subsequent loading or ion-exchange. For a 20% target loading of TMA(OH) onto the ZSM-5, 122.2 gms of 25% aqueous TMA(OH) was added into a vessel that was connected to an assembly that is similar to a rotary evaporator. The hot water bath was maintained at about 35° C. and the drying/evaporating process was conducted for about three hours at vacuum pressures between 12 and 31 mm Hg. The dried material was removed from the vessel and transferred to a flat dish for further drying in a vacuum desiccator. The drying in the vacuum desiccator was kept at 40° C. for about 15 hours. The resulting dried material was fluffy when dried. A coupling reaction test based on reacting aniline and nitrobenzene failed to show the presence of phenazine.

TMA(OH) Loading Example No. 6

164.3 gms of calcined and protonated ZSM-5 was added to a mixture of 131.4 gms of 25% aqueous TMA(OH) and 164 ml of deionized water. The solution was ion exchanged for several hours at 40° C. The slurry was filtered and the filtrate was set aside for future loadings. The filter cake was not subject to further drying, instead it was treated with 254.7 gms of 25% aqueous TMA(OH) for a 20% target loading of TMA(OH). The resulting slurry was dried in a rotary evaporator set-up for several hours until it was moist dry. The rotary evaporator was run at 35° C. and 11 to 35 mm Hg. The dried material was transferred to a flat dish and placed in a vacuum desiccator with an inert gas purge. The vacuum desiccator was maintained at 40° C. and drying was allowed for 4 days. The resulting dried material was hard, difficult to grind and consisted of what appeared to be two solid phases when ground. A coupling reaction test based on reacting aniline and nitrobenzene showed appreciable amounts of phenazine.

TMA(OH) Loading Example No. 7

195.4 gms of calcined and protonated ZSM-5 was added to a mixture of 156.3 gms of 25% aqueous TMA(OH) and 195 ml of deionized water. The solution was ion exchanged for three hours at 40° C. using a hot water bath. The slurry was filtered and the filtrate was set aside for future loadings and ion exchange. The filter cake was subjected to further drying in a vacuum desiccator that was equipped with a nitrogen purge. The drying in the vacuum desiccator was at 35° C. and maintained at that temperature for several hours (48 hours or less) for complete removal of the moisture. The dried material was treated with 216.3 gms of 25% aqueous TMA(OH) for a 20% target loading of TMA(OH). The resulting slurry was dried in a rotary evaporator set-up for several hours until it was moist dry. The rotary evaporator was run at 35° C. and 4 to 35 mm Hg. The dried material was transferred to a flat dish and placed in a vacuum desiccator with an inert gas purge. The vacuum desiccator is maintained at 40° C. and drying was allowed for several hours (48 hours or less). The resulting dried material was not hard, and easy to grind and consisted of what appears to be one phase when ground. A coupling reaction test based on reacting aniline and nitrobenzene failed to produce phenazine.

TMA(OH) Loading Example No. 8

This example is similar to TMA(OH) loading Example No. 7 except that the slurry contained 262.4 gms of calcined and protonated ZSM-5, 211.4 gms. Of 25% aqueous TMA (OH) and 262 ml of deionized water. The ion exchange was conducted at 40° C. for three hours. The filter cake after ion exchange was dried using a vacuum desiccator without a nitrogen purge overnight at room temperature. The drier cake was further dried in a vacuum desiccator at 35° C. for 2.5 hours using a nitrogen purge. For a 20% target loading of TMA(OH) onto the ZSM-5, 413.8 gms of 25% aqueous TMA(OH) was added into a vessel that was connected to an assembly that was similar to a rotary evaporator. The hot water bath was maintained at about 35° C. and the drying/ evaporating process was conducted for about 2.5 hours at vacuum pressures between 8 and 38 mm Hg. The dried material was removed from the vessel and transferred to a flat dish for further drying in a vacuum desiccator. The drying in the vacuum desiccator was kept at 40° C. for about 3 hours. The resulting dried material was not hard, and easy to grind and consisted of what appears to be one phase when ground. A coupling reaction test based on reacting aniline and nitrobenzene failed to produce phenazine.

The above examples indicate that the amount of the residual water in the loaded zeolite is critical to the success of the loading. Allowing material to be dried beyond the dihydrate within the zeolite channels will collapse the structure. It is estimated that for an optimum loading preparation the residual water in the ZSM-5 should be limited to a level corresponding to a range of from a pentahydrate down to a trihydrate.

For example:

In a 20% target loading of the base, the minimum residual water should be about 7.9% while at 25% loading of the base, the minimum is about 9.9% to avoid the risk of structural collapse.

The optimum upper limit for the residual water in the base loaded in the zeolite should correspond to a pentahydrate. For a 20% base loading this corresponds to a maximum residual water of 19.8% and for a 25% loading, the maximum residual loading is about 24.7%. It is believed that beyond these numbers, the loaded zeolite will require further drying during the coupling reaction which would increase the cycle time.

Estimate of Drying Time

Drying time is difficult to fix due to the differences in application of techniques in evaporation and final drying. However, it is clear from several examples (4,6,7 and 8) that there are two distinct stages in drying: One is the first "fast" stage where unbound water is liberated from the loaded zeolite until it reaches the more stable hydrate form of the base crystals within the intracrystalline channels.

Once an octahydrate is formed, the drying time slows down as more TMA(OH)-crystal bound water is taken away. This is the slow second drying stage. It is thought that the diffusion time for water out of the zeolite structure is not as critical as the release of water from the base crystals. An estimate of average drying time for loading example No. 8 shows the first stage to be about 1.107 gm/min, while in the slow second stage, the rate is about 0.5 gm/min.

Coupling Reaction

A series of coupling reaction experiments were conducted to evaluate the various loading techniques, the aniline to nitrobenzene ratio, pressure and temperature. In the following discussion, except in a few instances, the focus will be on well loaded materials, since the loaded materials which contained partial structural collapse produced marginal improvements on product selectivity.

In the course of the experiments, it was observed that even in a well mixed condition, the zeolite tends to settle at the bottom of the reactor for the lower aniline to nitrobenzene ratios. Note that ZSM-5 has a specific gravity of 1.8. It was determined that after a series of tests with a variety of aprotic solvents, the aspect ratio and the weight percent solids are important factors for achieving a well-mixed aniline—TMA (OH)/ZSM-5 slurry. For the 500 ml reactor, it was observed that a well mixed slurry with no solids settling can be achieved with an aspect ratio (aspect ratio=reaction mixture height/diameter)>0.79 at not greater than about 50 weight percent solids where the amount of zeolite charged is large. Moreover, it was observed that a simple mixing of calcined ZSM-5 in aniline and aqueous TMA(OH) does not produce a stable suspension. Even at a low loading of the aniline/

ZSM-5 slurry, the suspension agglomerates into large particles at 70° C. In time, the growth of particle agglomeration produces a material that has glue-like consistency and forms a striation-like structure in the liquid phase. After a half-hour of mixing, this striation-like material would eventually fall out of solution and strongly cling to the walls of the reaction vessel. This behavior was not found for a slurry of aniline and TMA(OH) loaded ZSM-5, where the stability of the slurry occurs for several days without significant setting. Therefore, the simple addition of zeolite to the aniline-TMA (OH) mixture does not produce the same effect as the loaded ZSM-5.

Slurry instability may also be caused by leaching of TMA(OH). In a separate experiment, 1-methyl-2-pyrolidinone was added to the aniline-TMA(OH)/ZSM-5 slurry. The addition caused the slurry suspension to become unstable and produces an effect similar to the one described above. It is surmised that 1-methyl-2-pyrolidinone extracts TMA(OH) away from the zeolite matrix. A well-suspended slurry of aniline-TMA(OH)/ZSM-5, therefore, indicates the absence of TMA(OH) leaching and also implies that the TMA salt of the aniline ion formed appears to reside inside the zeolite intracrystalline pores.

Following are examples of Coupling Reactions, beginning with Examples 1 and 2 that are concerned with studies of suspension stability. All reagents were used as received, unless otherwise stated, and all yields were determined by HPLC as recited. 4-NDPA and 4-NODPA are present in free form or as their salts.

Coupling Reaction, Example 1
Zeolite Suspension Stability 16.0 gms of 20% loading (by weight) of TMA(OH) on ZSM-5 was added to 15.9 gms of aniline. Vigorous mixing as high as 500 RPM was maintained to provide good suspension of the zeolite. After several minutes of mixing, the agitator was shut off to investigate the stability of the suspension. It was observed that for an aspect ratio of 0.79 or higher, the suspension can be made to be stable for at least 41 minutes.

If the temperature was dropped to around 35-40° C., the slurry became thick and difficult to mix, however, the suspension remained stable so long as the aspect ratio was greater than 0.79 and the stability was for about 41 minutes before significant settling of the zeolite was observed. In raising the temperature back to 70° C. or higher, the slurry thinned out and mixing became less difficult and suspension stability was maintained so long as the aspect ratio was greater than 0.79.

Coupling Reaction Example 2
Use of aprotic solvents
    Aniline/pyridine

In a mixture of 8.1 gms pyridine, 8.4 gms of aniline and 5.1 gms of 20% TMA(OH) loaded on ZSM-5 stability was poor above about 58° C. Below 58° C., the suspension was stable with aniline and pyridine mutually soluble. At temperatures greater than 58° C., TMA(OH) loaded on ZSM-5 drops out of phase and produces a separate viscous glue-like texture with which the coupling reaction can hardly occur.
    Aniline/Octane A mixture was made of 8.0 gms of octane, 8.3 gms of aniline and 4.9 gms of 20% TMA(OH). Octane and aniline are basically soluble in each other at 70° C., which is the typical coupling reaction temperature. However, when the TMA(OH) loaded ZSM-5 was slowly added to the hot aniline-octane mixture, octane separated out on top and the aniline preferred the TMA(OH) loaded ZSM-5. The temperature dropped. As temperature was increased, the volume of the octane phase increased and the TMA(OH) loaded ZSM-5 thickened to a viscous glue-like texture as a separate phase. At this point, there was hardly a coupling reaction with nitrobenzene.

Adding deionized water caused formation of three phases, namely: a water phase where most of the TMA(OH) loaded ZSM-5 was concentrated, an aniline phase and an octane phase.

1-methyl-2-pyrrolidione/Aniline

The function of certain solvents like those above can be surmised as extraction solvents to remove TMA(OH) encapsulated in a zeolite matrix. For example, in a mixture of 8.1 gms of 1-methyl-2-pyrolidinone, 8.4 gms of aniline and 4.8 gms of 25% aqueous TMA(OH), there is complete miscibility at room temperature. At temperatures as high as 75° C. the mixture is maintained as one phase. At these conditions, the coupling reaction between aniline and nitrobenzene proceeds at the usual reaction velocity.

In another example, 5.1 gms of 20% TMA(OH) loaded on ZSM-5 was added to 8.0 gms of 1-methyl-2-pyrolidinone and 8.1 gms of aniline. The resulting slurry was stable up until 65° C. Beyond 65° C., the ZSM-5 particles phased out and formed a thick material that had a consistency, as in the previous example, of a viscous glue-like texture.

In another example, 4.1 gms of calcined and protonated ZSM-5 was charged to a mixture of 16.0 gms of 1-methyl-2-pyrolidinone and 15.9 gms of aniline. This slurry appeared to be stable at 70° C. up to a point when 25% aqueous TMA(OH) was added, whereupon the zeolite separated out as a material with a viscous glue-like texture.

The results of example 2 show that certain solvents promote extraction of the organic base from the loaded ZSM-5, but aniline does not appear to extract base from the ZSM-5. However, the settling of solids may be a concern if the aspect ratio is less than 0.79 for an aniline only solvent. Other solvents that do not extract base from ZSM-5 would be suitable.

Coupling Reaction Example 3

A series of coupling reactions were conducted to show the effect of TMA(OH) levels. The reaction steps employed were similar to those disclosed in US Pat. No. 5,453,541, with certain exceptions. The first exception was a reaction vessel having dimensions such that the aspect ratio (height to diameter) was greater than 0.79 and there was a symmetric internal baffle to reduce vortex formation. The second exception was charging the reaction vessel with a dry solid prepared from several of the above examples comprising TMA(OH) loaded ZSM-5. Before the solid was charged to the liquid in the reaction vessel, the agitator was kept at high speed, typically between 200 to 500 RPM and heat was added to the slurry to reach a temperature typical of the reaction rate for the head-to-tail coupling of nitrobenzene. The solid was slowly added so that clumping was prevented. This was accomplished by a vibratory feed motion of solid into the reaction vessel and so that the solid was well distributed over the surface of the reaction media. Base drying was not necessary as the loaded TMA(OH) on ZSM-5 corresponded to very small amounts of water.

Typically, when prepared as above, the water of hydration for loaded TMA(OH) zeolite is less than about 5 moles of water per mole of tetramethyl-ammonium hydroxide at the start of the reaction. For comparison, when starting with 25% TMA(OH) the mixture must be dried from 15 moles to about 5 moles of water per mole of TMA(OH) before the reaction may proceed. Therefore, in all head-to-tail coupling of aniline and nitrobenzene using TMA(OH) loaded zeolite, base drying time is drastically reduced or completely eliminated and nitrobenzene addition may be immediately started as soon as all the loaded TMA(OH) zeolite is added to the reaction vessel. While nitrobenzene is being added, the vacuum system may be initiated and kept at 70 mm Hg or so to further remove the water.

Table I shows an example of a typical run. Table I also shows a product distribution comparison with a run that does not contain a TMA(OH) loaded ZSM-5 (Si/Al=0 and 0% TMA(OH) loading).

The molar ratios of AN/NB for the above coupling reactions are high. This is due to zeolite settling when lower ratios are used. For the reactions summarized in Table I, the aspect ratio is close to 2 with solids content that range from 6.3% to 13.6%. This is very low solids loading and therefore suggested the use of diluents/solvents to decrease the AN/NB ratio and still maintain slurry suspension. As shown in Coupling Reaction Example 2, some solvents may extract the base out of the zeolite. It was found, however, that if a critical aspect ratio is used a lower AN/NB ratio could be employed. This aspect ratio was found to be about 0.79.

TABLE III

| Coupling of Aniline and Nitrobenzene | |
|---|---|
| Wt % TMA(OH) | 28 |
| Mole Aniline/Nitrobenzene | 5.9 |
| Mole Aniline/Nitrobenzene | 1.05 |
| Temperature, ° C. | 70 |
| Pressure, mm Hg | 70 |
| Mole 4-NODPA/Mole 4-NDPA | 123.5 |
| wt % Phenazine | 0.04 |

Coupling Reaction No. 6

The use of a dried organic base that is encapsulated or loaded onto a zeolite matrix as that of ZSM-5 can alter the reaction pathways versus Stern's patent on coupling of aniline and nitrobenzene. The benefits of the organic base encapsulated with the zeolite matrix are 1.) high selectivity and 2.) significant reduction or elimination of azobenzene and total elimination of the formation of phenazine. FIG. 4 shows the kinetic pathway using a TMA(OH) loaded ZSM-

TABLE I

| % Solids in Slurry | Si/Al | TMA (OH) Loading Wt % | Mole Ratio of Aniline to Nitrobenzene | Mole Ratio of Nitrobenzene to Base | Temp. Deg C. | Press. mm Hg | Wt % Product Production | | | |
|---|---|---|---|---|---|---|---|---|---|---|
| | | | | | | | 4-NODPA | 4-NDPA | T-Azo | Phenazine |
| 6.31 | 50 | 21 | 21 | 3.1 | 70 | 60 | 86.57 | 13.43 | 0 | 0 |
| 7.54 | 50 | 20 | 34.4 | 1.68 | 70 | 60 | 87.39 | 12.61 | 0 | 0 |
| 13.6 | 50 | 25 | 23.3 | 1.01 | 70 | 60 | 91.11 | 8.89 | 0 | 0 |
| 0 | 0 | 0 | 26 | 1.9 | 70 | 60 | 94.22 | 4.62 | 0.74 | 0.42 |

Coupling Reaction Example No. 4

Using the above procedure and with a loading of TMA (OH) greater than 25% by weight onto ZSM-5, the product distribution showed appreciable levels of t-azobenzene and phenazine. This signified a collapse in the structure of the zeolite material and is evidenced as a dried solid product that appears to contain two separate solid phases. The result of the coupling reaction is shown in Table II.

TABLE II

| Coupling of Aniline and Effect of a Collapsed Zeolite | |
|---|---|
| Si/Al Ratio | 150 |
| Wt. % TMA(OH) | 29 |
| Mole Aniline/Nitrobenzene | 7.8 |
| Mole Nitrobenzene/Base | 1.97 |
| Temperature, ° C. | 70 |
| Pressure, mm Hg | 82 |
| 4-NODPA, wt % | 75.63 |
| 4-NDPA | 8.96 |
| t-Azo | 11.83 |
| Phenazine | 3.58 |

Coupling Reaction No. 5

Following the reaction steps as indicated in the coupling reaction examples above, a high loading of TMA(OH) but with lower molar ratio of aniline to nitrobenzene and lower nitrobenzene to base ratio was used. Table III shows the result and while the loading was relatively high, the structure did not have significant collapse in the zeolite structure and this is evidenced in a very small production of phenazine with no detected amounts of azobenzene. The very high ratio of 4-NODPA to 4-NDPA is indicative of a very significant reduction in hydrogenation cycle time since 4-NODPA hydrogenates much easier and quicker than 4-NDPA.

5. Table IV presents data relating to a typical coupling reaction run by this procedure.

TABLE IV

| Coupling of Aniline and Nitrobenzene | | |
|---|---|---|
| Wt % TMA(OH) | 20 | 20 |
| Mole Aniline/Nitrobenzene | 7.6 | 7.6 |
| Mole Nitrobenzene/Base | 1.05 | 1.05 |
| Temperature, ° C. | 70 | 70 |
| Pressure, mm Hg | 70 | 70 |
| Mole 4-NODPA/Mole 4-NDPA | 57.85 | 79.96 |
| wt % Phenazine | 0 | 0 |
| wt % Azobenzene | 0 | 0 |
| Nitrobenzene Conversion | 45 | 89.67 |
| Selectivity | 100 | 100 |

Coupling Reaction No. 7

The coupling reaction given in example 6 employs materials prepared from techniques established in TMA(OH) loading example No. 7. If the loading preparation does not allow sufficient pore-filling equilibration as in slow drying for several hours (48 hours), some organic base would settle on the crystal surface of the zeolite. Typical of these are high vacuum and high heat rate for rapid water evaporation. The effect of TMA(OH) deposits on the crystal surface resulting from inadequate equilibration may be observed in Table V which shows the presence of azobenzene and lower molar ratio of 4-NODPA to 4-NDPA compared to those given in the coupling reaction of Example 6. As previously mentioned, the importance of achieving a high molar ratio of 4-NODPA to 4-NDPA is that it yields a shorter time for hydrogenation of these tetra methyl ammonium salts.

TABLE V

Coupling of Aniline and Nitrobenzene

| | |
|---|---|
| Wt % TMA(OH) | 20 |
| Mole Aniline/Nitrobenzene | 7.6 |
| Mole Nitrobenzene/Base | 1.05 |
| Temperature, °C. | 70 |
| Pressure, mm Hg | 70 |
| Mole 4-NODPA/Mole 4-NDPA | 31.68 |
| wt % Phenazine | 0 |
| wt % Azobenzene | 0.15 |
| Nitrobenzene Conversion | 95.41 |
| Selectivity | 98.65 |

Coupling Reaction No. 8

The zeolite encapsulated organic base contains small amounts of moisture. A practical amount is equivalent to about a dihydrate of the organic base. It is believed that water of hydration less than the dihydrate may cause the zeolite structure to collapse. Because the amount of water is small, the coupling reaction may be conducted at higher pressure (there is no need to remove water) which allows a more direct one-step process for the production of 4-ADPA. Table VI shows an example of a comparison of low and high pressure where for about similar conversion, both pressures yield similar selectivity values.

TABLE VI

Coupling of Aniline and Nitrobenzene

| | | |
|---|---|---|
| Wt % TMA(OH) | 20 | 26.7 |
| Mole Aniline/Nitrobenzene | 7.6 | 7.89 |
| Mole Nitrobenzene/Base | 1.05 | 1.05 |
| Temperature, °C. | 70 | 90 |
| Pressure, mm Hg | 70 | 200 |
| Mole 4-NODPA/Mole 4-NDPA | 57.81 | 55.53 |
| Nitrobenzene Conversion | 45.94 | 42.4 |

Thermal Gravimetric Analysis (TGA)

Figure 6:
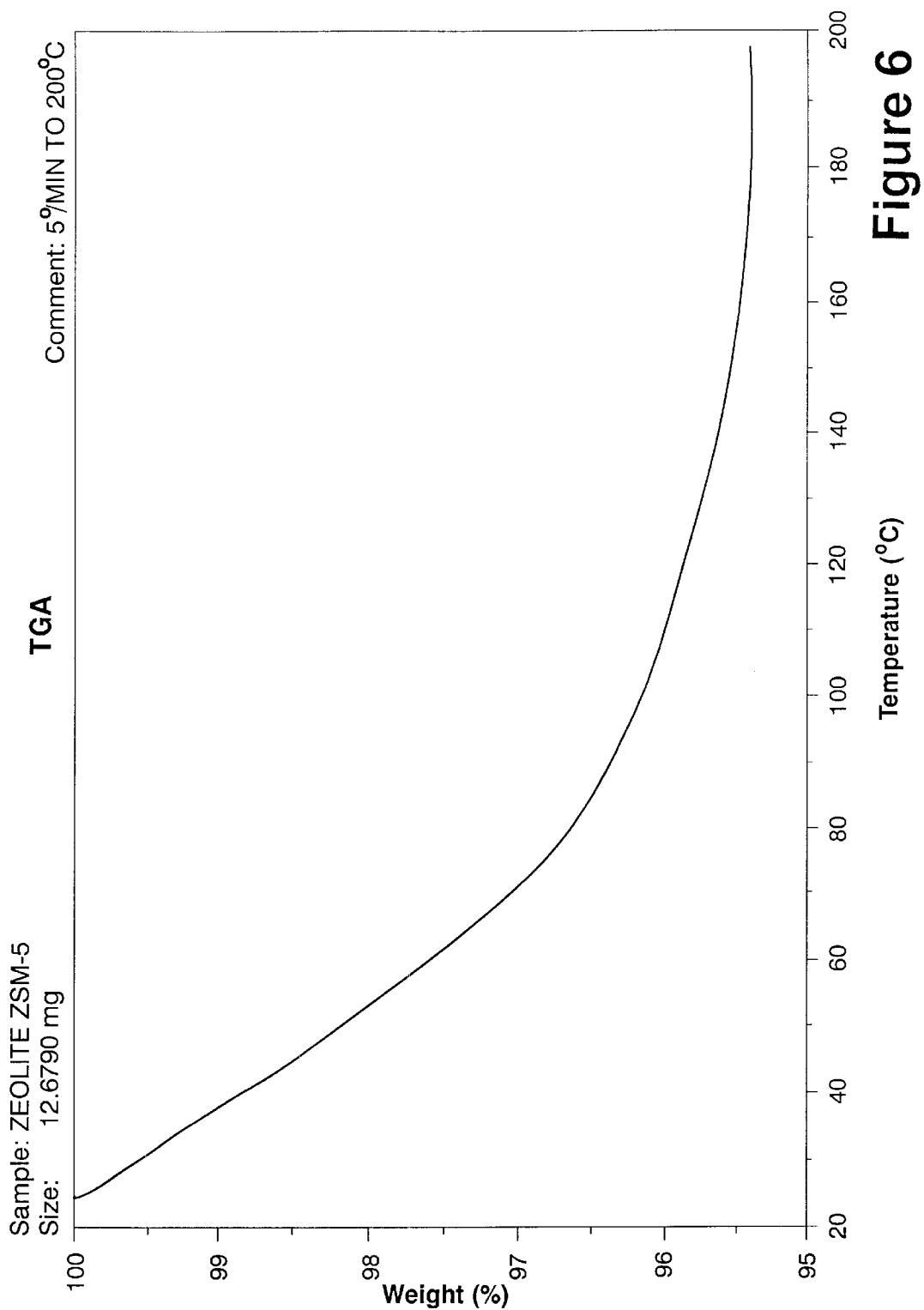
FIG. 6 shows a TGA (Thermal Gravimetric Analysis) curve for ZSM5.
Figure 9:
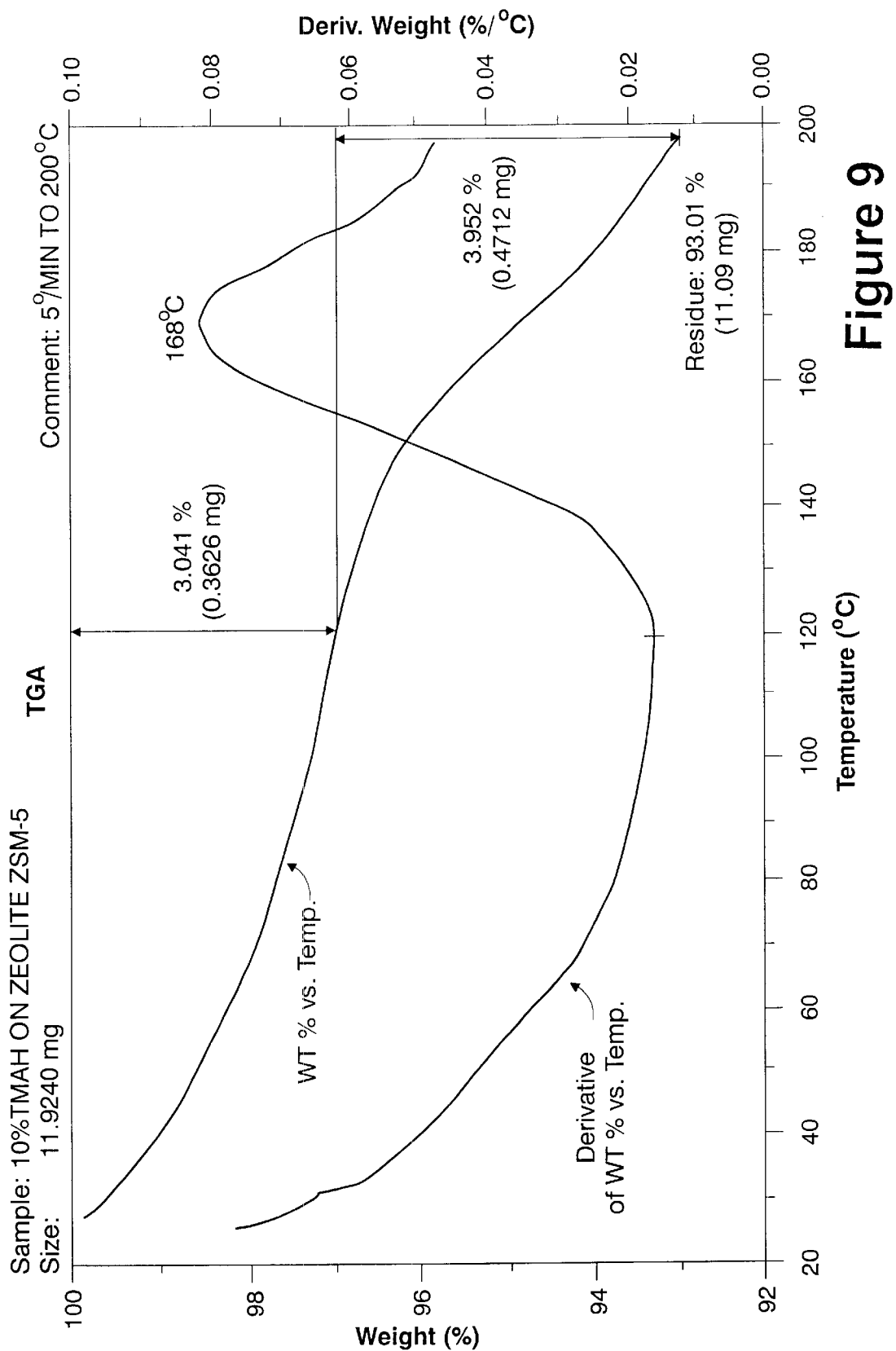
FIGS. 9, 10 and 11 show TGA curves for TMA(OH) on ZSM-5, 10, 15 and 25 wt. %, respectively.
Figure 10:
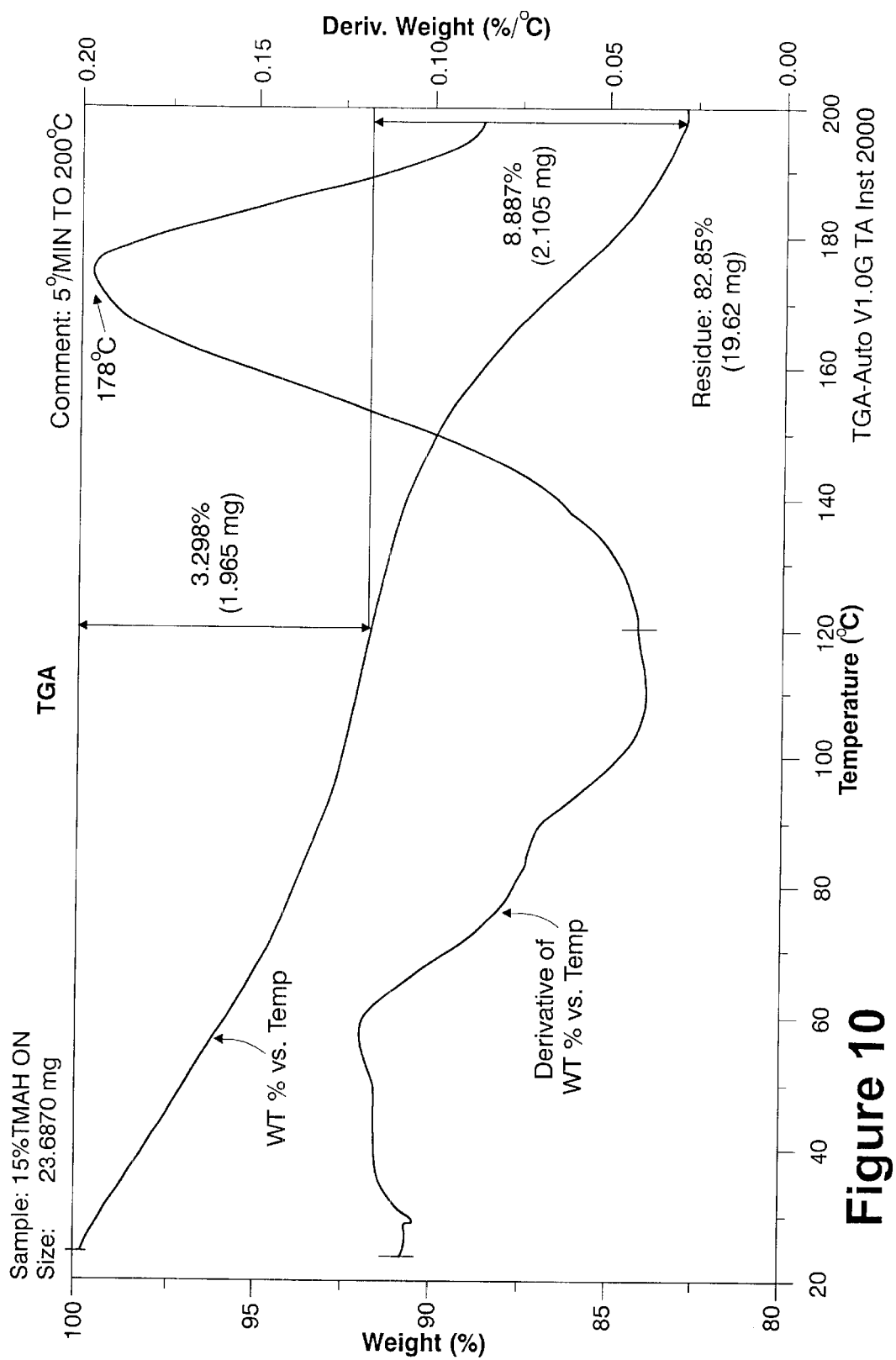
Figure 11:
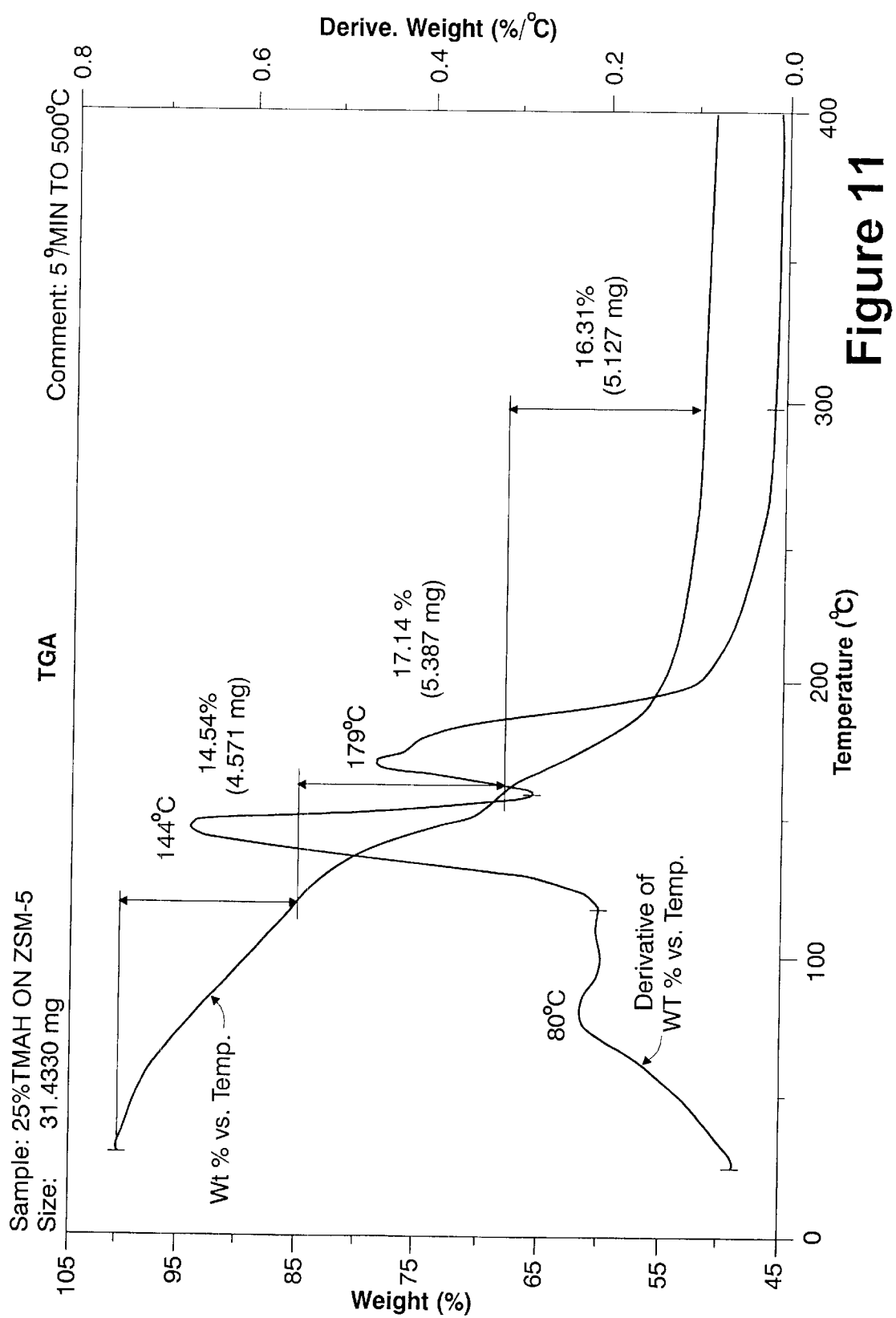

A TGA was conducted of the TMA(OH)loaded ZSM-5 to characterize the TMA (OH) loading and verify the amount of TMA (OH) deposited. Moreover, the TGA of ZSM-5 (FIG. 6), 25 (w) % TMA (OH) (FIG. 7) and TMA (OH) pentahydrate (FIG. 8) were obtained to provide a basis of comparison and analysis. FIGS. 9, 10 and 11 show typical TGA for TMA (OH) loaded ZSM-5 at 10%, 15% and 25% loadings, respectively. FIGS. 7–11 also show curves of the derivatives of the wt. % vs. temperature curves to clearly establish where peak temperatures occur.

All good loaded samples, i.e., samples that were prepared which do not show discernable structural collapse have characteristic TGA spectrums that have a narrow high temperature (over about 150° C.) range of multiple peaks (the β peaks). The peaks in the 25–to about 150° C. temperature range (the α peaks) are interpreted as the amount of water that was sorbed through sample handling and transfer, and small amounts of TMA (OH) decomposition. The amount of water in the just-prepared TMA (OH)/ZSM-5 is usually characterized similar to a pentahydrate. Estimates from the TGA spectrum suggests a 4.5 hydrate. The peaks that occur past 150° C., typically in the 180° C. temperature range (referred to as the β peaks), correspond to primarily a TMA (OH) decomposition, because at those temperatures, most of the water has been desorbed.. Hence, the weight loss in this temperature regime is approximately equal to weight loss at the β peaks. The presence of multiple peaks in the high temperature regime (the β peaks) may be caused either by diffusion or the difference in activation energy of TMA (OH) decomposition in the Zeolite (heterogeneous surface). The presence of stable TMA (OH) hydrates at those temperatures could also explain the existence of the multiple β peaks.

The TGA spectrum for aqueous 25 (w) % TMA (OH) reveals two distinct peaks, which suggests that the activation for the decomposition of TMA (OH) is dependent upon the amount of water present. The higher peak temperature decomposition (152° C.) corresponds to a less hydrated form of TMA (OH). The TGA spectrum for the pentahydrate is similar to the 25 (w) % TMA (OH), except that the β peak is 132° C. (20° C. lower than the 25(w) % TMA (OH)). This difference in the β peak temperatures can be accounted for by the decomposition of the most stable form of the TMA (OH) hydrate. For the pentahydrate, it can be estimated from the TGA spectrum that the most stable hydrate is TMA (OH)·2.3$H_2O$ at the β peak. The 2.3 moles $H_2O$ per mole TMA (OH) is perhaps a lower bound estimate because, some TMA (OH) could have decomposed at temperature less than 152° C., although this number should not deviate very much from the actual number. In a similar manner, for the 25 (w) % TMA (OH), the most stable hydrate is TMA (OH)·3.3$H_2O$.

Figure 7:
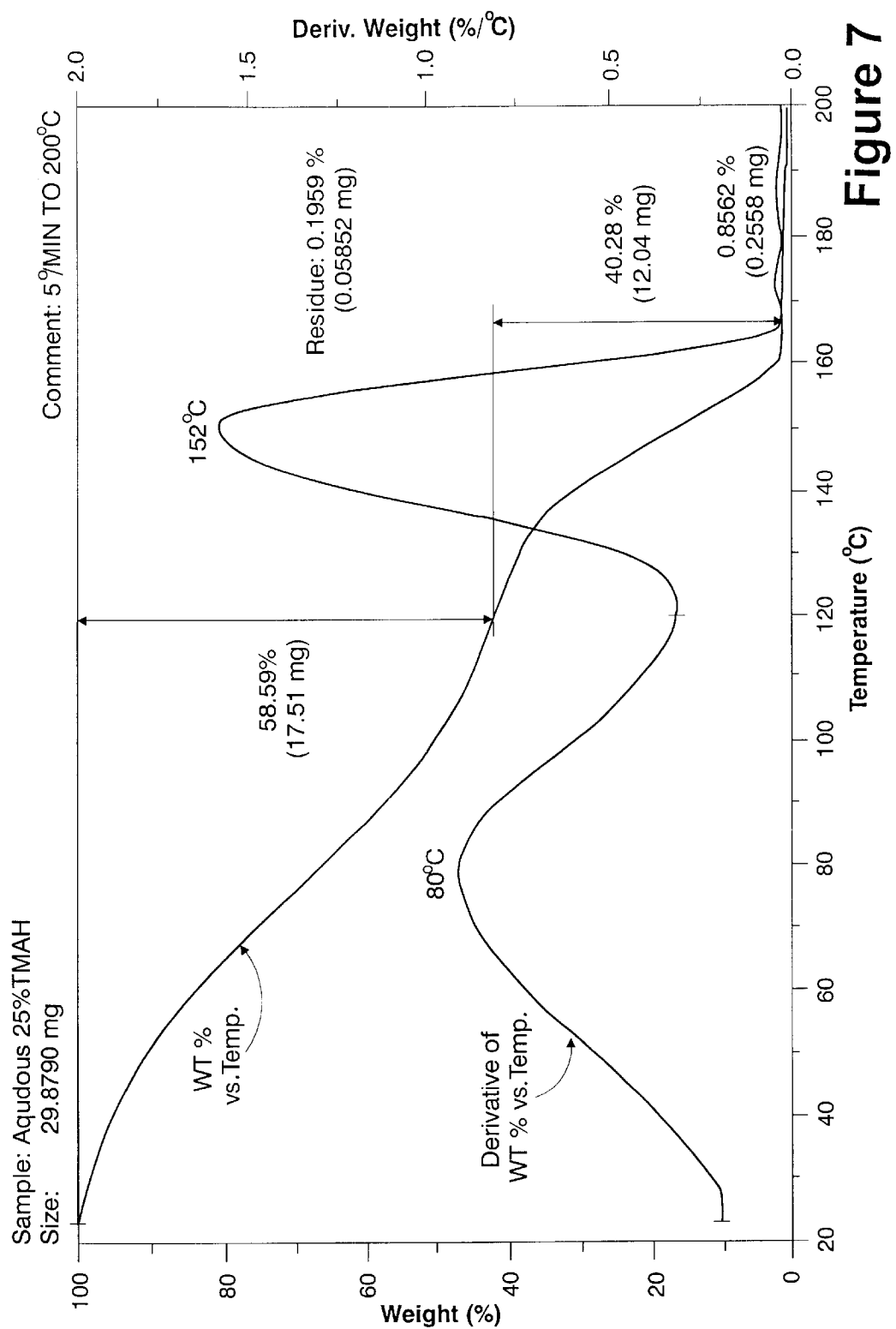
FIG. 7 shows TGA curves for aqueous 25wt. % TMA (OH).
Figure 8:
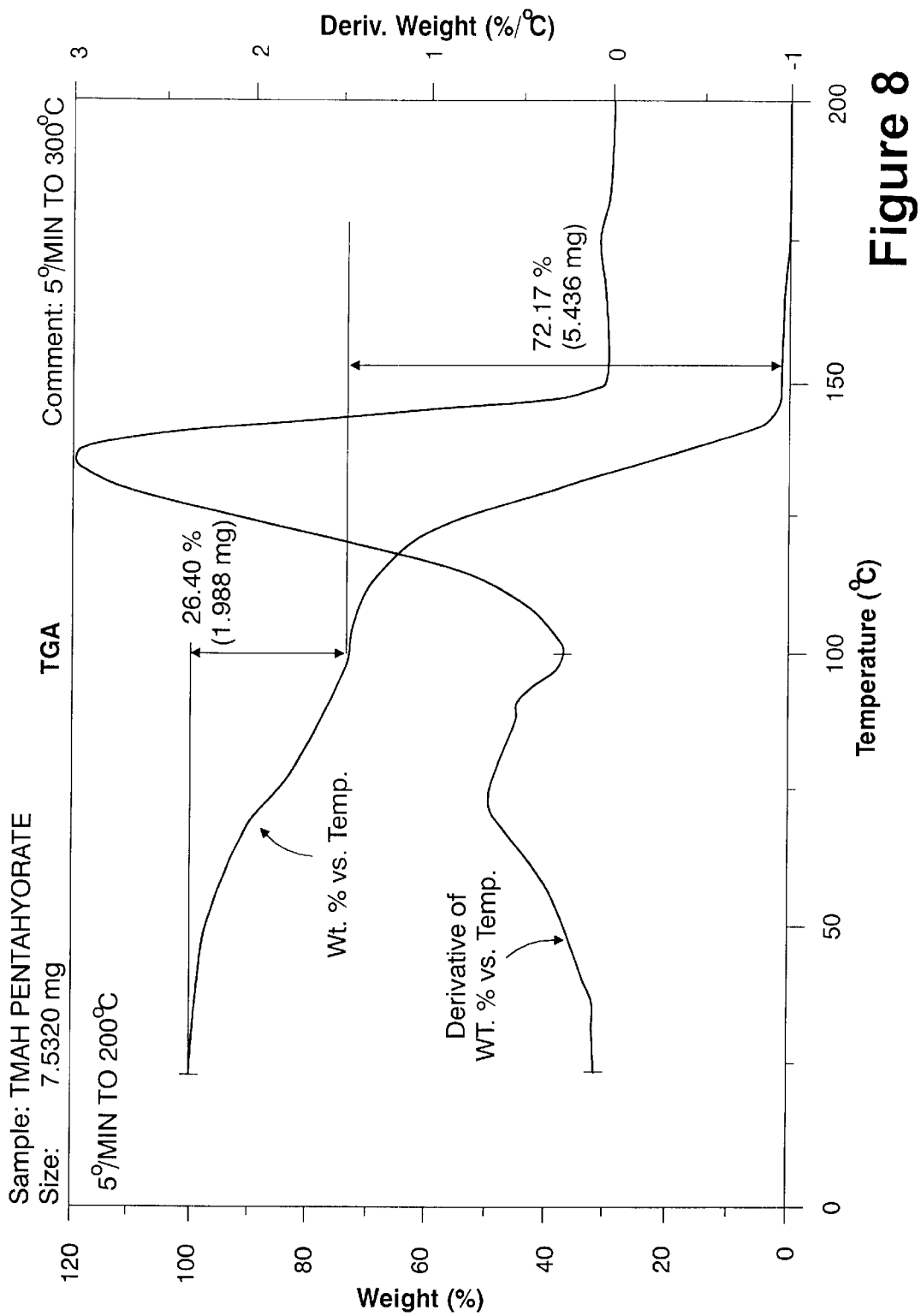
FIG. 8 shows TGA curves for TMA (OH) pentahydrate.

The α peak temperatures for the "free" TMA (OH) as shown in FIG. 7 does not vary significantly. For example, for the 25(w) % or 15.2 moles $H_2O$, the α peak temperature is at 80° C., while for the pentahydrate, it is about 75° C. with a shoulder at about 89° C. The α peak could be interpreted as the evaporation of unbound (or "excess") water with small amounts of TMA (OH) decomposition. These numbers also imply that once the unbound water is evaporated, the resulting hydrate is much more difficult to decompose, especially if the hydrate is of a lower form. The higher β peak temperatures as shown in following Table VII and FIGS. 9–11 for the TMA (OH)/ZSM-5 vs. free TMA.(OH) could imply that either TMA (OH) exists in its "almost free water state" or that the resulting TMA (OH)·x$H_2O$ is tightly bound inside the ZSM-5 intracrystalline channels, or both. Here x must be a small number, perhaps <2.3. It should be noted that as the loaded ZSM-5 gets thoroughly dried, structural collapse would occur as the temperature ramping progresses. But in spite of this structural collapse, the β peak temperature is nevertheless high, denoting a tightly bound TMA (OH).

TABLE VII

TGA RESULTS, TMA (OH)/ZSM-5

| Sample No. | α Peak Temp. C. | Weight % Loss α | β Peak Temp. C. | Weight % Loss β | % TMA(OH) Loading |
|---|---|---|---|---|---|
| 1. | 67, 100 | 15.62 | 181 | 27.6 | 26.8 |
| 2. | 81 | 22.47 | 188 | 25.98 | 28 |
| 3. | 80 | 22.63 | 187 | 25.31 | 23.7 |
| 4. | 72, 112 | 17.99 | 178 | 22.61 | 21.4 |

Infrared Spectroscopy (IR)

Figure 12:
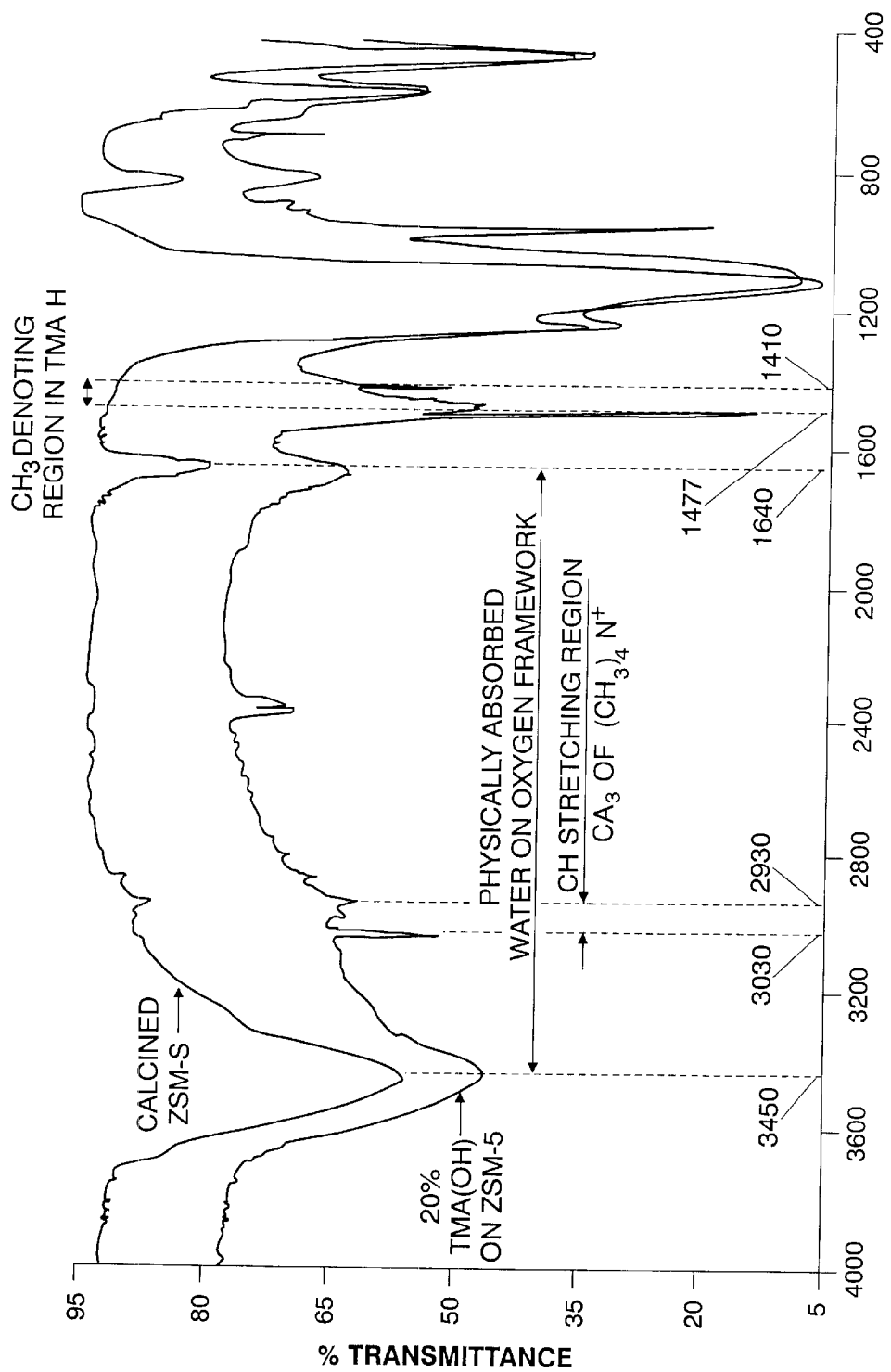
FIG. 12 presents IR spectroscopies of calcined ZSM-5 and TMA(OH) loaded ZSM-5.

IR pectroscopys of both calcined (protonated form) and the loaded ZSM-5 were obtained and are shown in FIG. 12. The IR specimens were not degassed so that water of absorption is visible in the IR spectra. Typically this occurs at 3450 and 1640 $cm^{-1}$, whethe physically absorbed water is on the oxygen framework. In a truly degassed material, the protonated form would show structural (or framework) hydroxyl groups at 3745 $cm^{-1}$ for the terminal silanol (SiOH), exhibiting very weak acidity and another IR band at 3610 $cm^{-1}$ for the Si-OH-Al groups, exhibiting very strong acidity.

In comparing the IR spectra of the loaded versus unloaded zeolite, it shows that a few IR bands appear for the loaded material on top of those that correspond to the unloaded material. The new IR bands represent the CH stretching region for $CH_3$ in $(CH_3)_4N^+$ at 3030 and 2930 cm⁻, and the $CH_3$ bending region at 1477 and 1410 cm⁻. These IR bands imply the presence of TMA (OH). Other IR bands at 750, 950 and 2400 cm⁻, although with relatively weak intensities, do not have at this time spectral assignments, and no interpretation can be attributed to these bands.

We claim:

1. A composition suitable for use in a reaction zone where aniline is reacted with nitrobenzene to obtain intermediates of 4-aminodiphenylamine (4-5 ADPA) comprising a solid support having interior channels with base material employed in the reaction loaded into said channels, the cross-sectional dimensions of said channels being such as to provide a restricted transition state with regard to the reaction and to improve the selectivity of the reaction in favor of said intermediates.

2. The composition of claim 1 wherein said support is selected from the group consisting of pillared clays, aluminosilicates and silica alumina phosphates.

3. The composition of claim 2 wherein said support comprises a zeolite.

4. The composition of claim 3 wherein said support comprises a ZSM-5 zeolite.

5. The composition of claim 1 wherein the base material is selected from the group consisting of $C_1$–$C_6$ alkoxides, quaternary ammonium hydroxides and mixtures thereof.

6. The composition of claim 1 wherein the base material is selected from the group consisting of inorganic bases selected from the group consisting of alkali metal hydroxides and mixtures thereof, and organic bases selected from the group consisting of strong alkali metal alkoxide bases, tetra substituted ammonium hydroxides and mixtures thereof, each substituent of an organic base source being independently selected from alkyl, aryl, arylalkyl trialkylammonium hydroxides, arylalkyl trialkylammonium hydroxides and alkylsubstituted diammonium hydroxides.

7. The composition of claim 1 wherein said base materials are used in conjunction with a phase transfer catalyst.

8. The composition of claim 7 wherein said phase transfer catalyst is selected from the group consisting of aryl, alkyl and aryl alkyl ammonium salts, crown ethers, and amine bases.

9. The composition of claim 4 wherein the base material is a strong organic base.

10. The composition of claim 9 wherein the strong organic base is tetramethylammonium hydroxide (TMA(OH)).

11. The composition of claim 10 wherein TMA(OH) comprises not greater than about 25 wt. % of said composition.

12. A method of making the composition of claim 3 comprising:
   (a) ion exchanging said zeolite with said base material by contacting said zeolite with an aqueous solution of said base material;
   (b) drying zeolite recovered from step (a);
   (c) adding additional base material in aqueous solution to the dried zeolite from step (b) to obtain zeolite slurry; and
   (d) recovering zeolite from said zeolite slurry having the desired loading of base material.

13. The method of claim 12 wherein said zeolite is ZSM-5 and said base material is TMA(OH), said slurry of step (c) being prepared by adding a sufficient amount of TMA(OH) solution, having a TMA(OH) concentration of not greater than about 28wt. %, to the dried ion-exchanged ZSM-5 at a temperature not greater than about 40° C. to obtain a loading of TMA(OH) on the ZSM-5 zeoite of not greater than about 25 wt. % and drying at a temperature not exceeding about 40° C. to obtain a TMA(OH) loaded ZSM-5 zeolite with a water to base mole ratio in the loaded TMA(OH) of from about 2.0 to about 5.0.

14. A composition prepared by the method of claim 12.

15. A process for the generation of intermediates of 4-ADPA comprising reacting aniline with nitrobenzene in a reaction zone, said reaction zone containing a solid support loaded with a base material, said solid support having interior channels with base material employed in the reaction loaded into said channels, the cross-sectional dimensions of said channels being such as to provide a restricted transition state with regard to the reaction and to improve the selectivity of the reaction in favor of said intermediates.

16. The process of claim 15 wherein said support is selected from the group consisting of pillared clays, aluminosilicates and silica alumina phosphates.

17. The process of claim 16 wherein said support comprises a zeolite.

18. The process of claim 17 wherein said support comprises a ZSM-5 zeolite.

19. The process of claim 18 wherein the amount of solids in the reaction mixture is not greater than about 50 wt. % and the aspect ratio in the reactor is greater than about 0.79.

20. The process of claim 15 wherein the base material is selected from $C_1$–$C_6$ alkoxides and quaternary ammonium hydroxides.

21. The process of claim 15 wherein the base material is selected from the group consisting of inorganic bases selected from the group consisting of alkali metal hydroxides and mixtures thereof, organic bases selected from the group consisting of potassium t-butoxide, alkoxides, quaternary amine hydroxides and organic bases selected from the group consisting of tetra substituted ammonium hydroxides, each substituent of which may be independently selected from alkyl, aryl or arylalkyl groups, aryl trialkylammonium hydroxides, arylalkyl trialkylammonium hydroxides and alkylsubstituted diammonium hydroxides.

22. The process of claim 15 wherein said base materials are used in conjunction with a phase transfer catalyst.

23. The composition of claim 22 wherein said phase transfer catalyst is selected from the group consisting of aryl, alkyl and aryl alkyl ammonium salts, crown ethers, and amine bases.

24. The process of claim 18 wherein the base material is tetramethylammonium hydroxide (TMA(OH)).

25. The process of claim 15 wherein the molar ratio of nitrobenzene to the base material is not greater than about 18.0.

26. A one-step process for preparing 4-aminodiphenylamine (4-ADPA) comprising charging nitrobenzene into a reaction zone under hydrogen pressure and in the presence of a base material loaded on a solid support and a hydrogenation catalyst, said solid support having interior channels with base material employed in the reaction loaded into said channels, the cross-sectional dimensions of said channels being such as to provide a restricted transition state with regard to the reaction and to improve the selectivity of the reaction in favor of 4-ADPA.

27. The process of claim 26 wherein the 4-ADPA is further reductively alkylated to produce alkylated paraphenylenediamine.

28. The process of claim 26 wherein the base material is selected from $C_1$–$C_6$ alkoxides and quaternary ammonium hydroxides.

29. The process of claim 26 wherein the base material is selected from the group consisting of inorganic bases selected from the group consisting of alkali metal hydroxides and mixtures thereof, organic bases selected from the group consisting of potassium t-butoxide, alkoxides, quaternary amine hydroxides and organic bases selected from the group consisting of tetra substituted ammonium hydroxides, each substituent of which may be independently selected from alkyl, aryl or arylalkyl groups, aryl trialkylammonium hydroxides, arylalkyl trialkylammonium hydroxides and alkylsubstituted diammonium hydroxides.

30. The process of claim 26 wherein said base materials are used in conjunction with a phase transfer catalyst.

31. The process of claim 30 wherein said phase transfer catalyst is selected from the group consisting of aryl, alkyl and aryl alkyl ammonium salts, crown ethers, and amine bases.

32. The process of claim 26 wherein the base material is tetramethylammonium hydroxide.

33. The process of claim 32 wherein the molar ratio of nitrobenzene to tetramethylammonium hydroxide is not greater than about 18.0.

34. The process of claim 26 wherein aniline is charged to the reaction zone such that said process is carried out in an excess of aniline.

35. The process of claim 34 wherein the molar ratio of aniline to nitrobenzene is not less than about 5.0.

36. The process of claim 26 wherein the hydrogenation catalyst is separate from said base material loaded on a solid support and comprises at least one of copper, silver-magnesium oxide, copper-cerium oxide, copper-manganese oxide, iron-manganese oxide, platinum, nickel, molybdenum, palladium, or sulfided noble metals, said metal being present on a suitable support selected from the group consisting of alumina, pumice, silica, activated carbon, and carbon black.

37. The process of claim 26 wherein said support comprises a zeolite.

38. The process of claim 37 wherein said support comprises ZSM-5.

39. The process of claim 38 wherein the amount of solids in the reaction mixture is not greater than about 50 wt. % and the aspect ratio in the reactor is greater than about 0.79.

40. The process of claim 26 wherein said solid support comprises a cylindrical extrudate having a hollow section along the longitudinal axis with the remainder of the extrudate comprising a structure with said base loaded interior channels, said hollow section being loaded with said hydrogenation catalyst.

41. The process of claim 40 wherein said hydrogenation catalyst comprises free metal loaded into said interior channels of said solid support with said base material.

42. A process for the hydrogenation of nitrobenzene to 4-aminodiphenylamine (4-ADPA) comprising:

(a) preparing a reaction zone by supplying a strong organic base loaded on a solid support and a hydrogenation catalyst, said solid support having interior channels with base material employed in the reaction loaded into said channels, the cross-sectional dimensions of said channels being such as to provide a restricted transition state with regard to the reaction and to improve the selectivity of the reaction favor of 4-ADPA;

(b) applying a flow of hydrogen at a pressure sufficient to force the conversion of nitrobenzene to 4-ADPA intermediates and to further hydrogenate the intermediates to 4-ADPA;

(c) charging to the reaction zone an amount of aniline and nitrobenzene such that the molar ratio of aniline to nitrobenzene in the reaction zone is not greater than about 5.0, and that the molar rat of nitrobenzene to the strong organic base is not greater than about 18.0; and (d) conducting the hydrogenation reaction for the conversion of nitrobenzene to 4-ADPA as a one-step process.

43. The process of claim 42 wherein the nitrobenzene is charged to the reaction zone on a continuous basis.

44. The process of claim 42 wherein the 4-ADPA is further reductively alkylated to produce alkylated paraphenylenediamine.

45. The process of claim 42 wherein the base material is selected from $C_1$–$C_6$ alkoxides and quaternary ammomium hydroxides.

46. The process of claim 42 wherein the base material is selected from the group consisting of inorganic bases selected from the group consisting of alkali metal hydroxides and mixtures thereof, organic bases selected from the group consisting of potassium t-butoxide, alkoxides, quaternary amine hydroxides and organic bases selected from the group consisting of tetra substituted ammonium hydroxides, each substituent of which may be independently selected from alkyl, aryl or arylalkyl groups, aryl trialkylammonium hydroxides, arylalkyl trialkylammonium hydroxides and alkylsubstituted diammonium hydroxides.

47. The process of claim 42 wherein said base materials are used in conjunction with a phase transfer catalyst.

48. The process of claim 47 wherein said phase transfer catalyst is selected from the group consisting of aryl, alkyl and aryl alkyl ammonium salts, crown ethers, and amine bases.

49. The process of claim 42 wherein the base material is tetramethylammonium hydroxide.

50. The process of claim 42 wherein aniline is charged to the reaction zone such that said process is carried out in an excess of aniline.

51. The process of claim 42 wherein the hydrogenation catalyst is separate from said base material loaded on a solid support and comprises at least one of copper, silver-magnesium oxide, copper-cerium oxide, copper-manganese oxide, iron-manganese oxide, platinum, nickel, molybdenum, palladium, rhodium, ruthenium, iridium and sulfided noble metals, said metal being present on a suitable support selected from the group consisting of alumina, pumice, silica, activated. carbon, and carbon black.

52. The process of claim 42 wherein the process is carried out as a continuous process and a fixed bed of hydrogenation catalyst is fed continuously with a charge of excess aniline, nitrobenzene, hydrogen and the strong organic base loaded on a solid support.

53. The process of claim 42 wherein nitrobenzene is charged to the reaction zone gradually over a period of time sufficient to achieve high selectivity to 4-ADPA and a charge of aniline is charged to the rection zone initially with the nitrobenzene.

54. The process of claim 42 wherein the process is carried out in the batch mode and the entire charge of nitrobenzene is supplied to the reaction zone at one time.

55. The process of claim 42 wherein said support comprises a zeolite.

56. The process of claim 55 wherein said support comprises ZSM-5.

57. The process of claim 56 wherein the amount of solids in the reaction mixture is not greater than about 50 wt. % and the aspect ratio in the reactor is greater than about 0.79.

58. The process of claim 42 wherein said solid support comprises a cylindrical extrudate having a hollow section along the longitudinal axis with the remainder of the extrudate comprising a structure with said base loaded interior channels, said hollow section being loaded with said hydrogenation catalyst.

59. The process of claim 15 wherein said intermediates of 4-ADPA that are generated in said reaction zone are converted to 4-ADPA in a second reaction zone by a catalytic hydrogenation reaction.

* * * * *